(12) United States Patent
Kain et al.

(10) Patent No.: US 11,697,847 B2
(45) Date of Patent: *Jul. 11, 2023

(54) SUPER RESOLUTION IMAGING

(71) Applicant: Illumina, Inc., San Diego, CA (US)

(72) Inventors: Robert C. Kain, San Diego, CA (US); Tarun Khurana, Fremont, CA (US); Kevin L. Gunderson, Encinitas, CA (US); Yir-Shyuan Wu, Albany, CA (US)

(73) Assignee: ILLUMINA, INC., San Diego, CA (US)

( * ) Notice: Subject to any disclaimer, the term of this patent is extended or adjusted under 35 U.S.C. 154(b) by 459 days.

This patent is subject to a terminal disclaimer.

(21) Appl. No.: 16/837,463

(22) Filed: Apr. 1, 2020

(65) Prior Publication Data

US 2020/0224267 A1 Jul. 16, 2020

Related U.S. Application Data

(63) Continuation of application No. 16/247,949, filed on Jan. 15, 2019, now abandoned, which is a
(Continued)

(51) Int. Cl.
*G01N 21/64* (2006.01)
*C12Q 1/6825* (2018.01)
(Continued)

(52) U.S. Cl.
CPC ......... *C12Q 1/6874* (2013.01); *C12Q 1/6825* (2013.01); *C12Q 1/6837* (2013.01); *G01N 21/6454* (2013.01)

(58) Field of Classification Search
None
See application file for complete search history.

(56) References Cited

U.S. PATENT DOCUMENTS 5,442,207 A 8/1995 Jeong
6,355,431 B1 3/2002 Chee et al.
(Continued)

FOREIGN PATENT DOCUMENTS

EP 2192401 6/2010
WO 1991/006678 5/1991
(Continued)

OTHER PUBLICATIONS

Ala-Kleme, et al, "Hot Electron-Induced Electrogenerated Chemiluminescence of Ru(bpy)32+ Chelate at Oxide-Covered Aluminum Electrodes," Analytical Chemistry 71 (24), 1999, 5538-5543.
(Continued)

*Primary Examiner* — Robert T. Crow
(74) *Attorney, Agent, or Firm* — Illumina, Inc.

(57) ABSTRACT

A detection apparatus that includes (a) an array of responsive pads on a substrate surface; (b) an array of pixels, wherein each pixel in the array has a detection zone on the surface that includes a subset of at least two of the pads; and (c) an activation circuit to apply a force at a first and second pad in the subset, wherein the activation circuit is configured to apply a different force at the first pad compared to the second pad, and wherein the activation circuit has a switch to selectively alter the force at the first pad and the second pad.

19 Claims, 7 Drawing Sheets

Related U.S. Application Data continuation of application No. 14/213,340, filed on Mar. 14, 2014, now abandoned, which is a continuation-in-part of application No. 13/835,492, filed on Mar. 15, 2013, now Pat. No. 9,193,998.

(60) Provisional application No. 61/788,954, filed on Mar. 15, 2013.

(51) Int. Cl.
*C12Q 1/6874* (2018.01)
*C12Q 1/6837* (2018.01)

(56) References Cited

U.S. PATENT DOCUMENTS

| | | | |
|---|---|---|---|
| 6,576,424 | B2 | 6/2003 | Fodor et al. |
| 6,890,741 | B2 | 5/2005 | Fan et al. |
| 6,913,884 | B2 | 7/2005 | Stuelpnagel et al. |
| 7,034,873 | B2 | 4/2006 | Mendis et al. |
| 7,057,026 | B2 | 6/2006 | Barnes et al. |
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,329,860 | B2 | 2/2008 | Feng et al. |
| 7,405,281 | B2 | 7/2008 | Xu et al. |
| 7,582,420 | B2 | 9/2009 | Oliphant et al. |
| 7,595,883 | B1 | 9/2009 | El Gamal et al. |
| 8,241,573 | B2 | 8/2012 | Banerjee et al. |
| 8,244,479 | B2 | 8/2012 | Kain et al. |
| 8,277,628 | B2 | 10/2012 | Ronaghi et al. |
| 9,193,998 | B2 * | 11/2015 | Khurana .............. G01N 27/27 |
| 9,202,835 | B2 | 12/2015 | Ozcan et al. |
| 2002/0012930 | A1 | 1/2002 | Rothberg et al. |
| 2002/0156593 | A1 * | 10/2002 | Hayes .................. G06K 9/0002 702/127 |
| 2003/0219891 | A1 * | 11/2003 | Yazawa ................ C12Q 1/6825 435/287.2 |
| 2004/0211659 | A1 | 10/2004 | Velev |
| 2005/0053980 | A1 | 3/2005 | Gunderson et al. |
| 2005/0181440 | A1 | 8/2005 | Chee et al. |
| 2005/0191698 | A1 | 9/2005 | Chee et al. |
| 2007/0075922 | A1 | 5/2007 | Jessop |
| 2008/0108082 | A1 | 5/2008 | Rank et al. |
| 2009/0032401 | A1 | 2/2009 | Ronaghi et al. |
| 2009/0046952 | A1 * | 2/2009 | Ben-Ezra .............. G06T 3/4053 382/299 |
| 2009/0186349 | A1 | 7/2009 | Gunderson et al. |
| 2009/0272914 | A1 | 11/2009 | Feng et al. |
| 2010/0009871 | A1 | 1/2010 | Reed et al. |
| 2010/0111768 | A1 | 5/2010 | Banerjee et al. |
| 2011/0059865 | A1 | 3/2011 | Smith et al. |
| 2011/0234757 | A1 | 9/2011 | Zheng et al. |
| 2011/0311980 | A1 | 12/2011 | Pollack et al. |
| 2012/0053063 | A1 | 3/2012 | Rigatti et al. |
| 2012/0270305 | A1 | 10/2012 | Reed et al. |
| 2013/0116128 | A1 | 5/2013 | Shen et al. |
| 2013/0116153 | A1 | 5/2013 | Bowen et al. |
| 2013/0260372 | A1 | 10/2013 | Buermann et al. |
| 2013/0338042 | A1 | 12/2013 | Shen et al. |
| 2014/0079923 | A1 | 3/2014 | George et al. |

FOREIGN PATENT DOCUMENTS

| | | |
|---|---|---|
| WO | 2004/018497 | 3/2004 |
| WO | 2005/065814 | 7/2005 |
| WO | 2007/123744 | 11/2007 |
| WO | 2009/012112 | 1/2009 |
| WO | 2012/054351 | 4/2012 |
| WO | 2013/070627 | 5/2013 |

OTHER PUBLICATIONS

Ala-Kleme, et al., "Near-infrared electrogenerated chemiluminescence of ytterbium(III) chelates in aqueous electrolytes," Analytical Chimica Acta 395, 1999, 205-211.

Bentley, et al., "Accurate whole human genome sequencing using reversible terminator chemistry," Nature, vol. 456, No. 7218, Nov. 6, 2008, 53-59.

Fromherz, et al., "ANNINE-6plus, a voltage-sensitive dye with good solubility, strong membrane binding and high sensitivity," Eur Biophys J. 37(4), 2008, 509-514.

Jiang, et al., "Cathodic electrogenerated chemiluminescence of Ru(bpy)32+ chelate at oxide-coated heavily doped silicon electrodes," Analytica Chimica Acta 541, 2005, 159-165.

Kulmala, et al., "Cathodic Electrogenerated Chemiluminescence of Luminol at Disposable Oxide-Covered Aluminum Electrodes," Analytical Chemistry 6, 1998, 1112-1118.

Kulmala, et al., "Energetic electrochemiluminescence of(9-fluorenyl)methanol induced by injection of hot electronsinto aqueous electrolyte solution," Journal of the Chemical Society, Faraday Transactions 93, 1997, 3107-3113.

Kulmala, "Hot electron-induced electrogenerated chemiluminescence of rare earth(III) chelates at oxide-covered aluminum electrodes," Journal of Fluorescence 8, 1998, 59-65.

Laakso, et al., "Hot electron-induced electrogenerated chemiluminescence of SYBR® Green I," Analytica Chimica Acta 541, 2005, 85-89.

Olympus, "Fluorescence Resonance Energy Transfer (FRET) Microscopy," http://www.olympusfluoview.com/applications/fretintro.html, 2009, 1-16.

Pourmand, et al., "Direct electrical detection of DNA synthesis," Proc. Natl. Acad. Sci. vol. 103, No. 17, Apr. 25, 2006, 6466-6470.

Rant, et al., "Dynamic electrical switching of DNA layers on a metal surface," Nano Letters, American Chemical Society 4(12), 2441-2445.

So, et al., "Fluorescence Spectrophotometry," Encyclopedia of Life Sciences, 2002, 1-4.

Stengel, "Surface plasmon field-enhanced fluorescence spectroscopy studies of primer extension reactions," Nucleic Acids Research, 33(7), 2005, e69-e69.

Suomi, et al., "Time-resolved detection of electrochemiluminescence of luminol," Analytica Chimica Acta 541, 2005, 167-169.

\* cited by examiner

A

B

C

SUPER RESOLUTION IMAGING

CROSS-REFERENCE TO RELATED APPLICATIONS

This application is a continuation of U.S. application Ser. No. 16/247,949, filed on Jan. 15, 2019, which is a continuation of U.S. application Ser. No. 14/213,340, filed on Mar. 14, 2014, which is a continuation-in-part of U.S. application Ser. No. 13/835,492, filed Mar. 15, 2013, now U.S. Pat. No. 9,193,998, which is based on, and claims the benefit of, U.S. Provisional Application No. 61/788,954, filed Mar. 15, 2013, each of which is incorporated herein by reference in its entirety.

BACKGROUND

Embodiments of the present disclosure relate generally to biological or chemical analysis and more particularly to systems and methods using detection devices for biological or chemical analysis.

Various protocols in biological or chemical research involve performing a large number of controlled reactions on local support surfaces or within predefined reaction chambers. The desired reactions may then be observed or detected and subsequent analysis may help identify or reveal properties of chemicals involved in the reaction. For example, in some multiplex assays, unknown analytes having identifiable labels (e.g., fluorescent labels) may be exposed to thousands of known probes under controlled conditions. Each known probe may be deposited into a corresponding location on a surface. Observing any chemical reactions that occur between the known probes and the unknown analyte on the surface may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. The resolution of standard imaging techniques is constrained by the number of pixels available in the detection device, among other things. As such, these optical systems can be relatively expensive and require a relatively large bench-top footprint when detecting surfaces having large collections of analytes. For example, nucleic acid arrays used in genotyping, expression, or sequencing analyses can require detection of millions of different sites on the array per square centimeter. Limits in resolution increase cost and decrease accuracy of these analyses Thus, there exists a need for higher resolution apparatus and methods, for example, to detect nucleic acid arrays. The present disclosure addresses this need and provides other advantages as well.

BRIEF SUMMARY

The present disclosure provides a detection apparatus that includes (a) an array of responsive pads on a substrate surface; (b) an array of pixels, wherein each pixel in the array has a detection zone on the surface that includes a subset of at least two of the responsive pads; and (c) an activation module to alter a characteristic of a first pad in the subset and of a second pad in the subset, wherein the activation module is configured to apply a different characteristic at the first pad compared to the second pad, and wherein the activation module has a switch to selectively alter the characteristic at the first pad compared to the second pad.

In particular embodiments, a detection apparatus can include (a) an array of electrically responsive pads on a substrate surface; (b) an array of pixels, wherein each pixel in the array has a detection zone on the surface that includes a subset of at least two of the electrically responsive pads; and (c) an activation circuit to apply an electric field at a first pad in the subset and a second pad in the subset, wherein the activation circuit is configured to apply a different electric field at the first pad compared to the second pad, and wherein the activation circuit has a switch to selectively alter the electric field at the first pad compared to the second pad.

The disclosure also provides a nucleic acid sequencing system. The system can include (a) a detection apparatus having (i) an array of responsive pads on a substrate surface; (ii) an array of pixels, wherein each pixel in the array has a detection zone on the surface that includes a subset of pads; and (iii) an activation module to alter a characteristic of the pads in the subset individually, wherein the activation module is configured to apply a different characteristic to a first pad of the subset compared to the other pads of the subset; (b) a readout circuit to acquire signals from the array of pixels; (c) a control module that directs the readout circuit to acquire signals from each of the pixels during a sensing period and that directs the activation module to sequentially apply different characteristic at the pads during the sensing period; and (c) a processing module that correlates (i) the signals acquired from the pixels during the sensing period and (ii) the sequential application of the different characteristics at the pads during the sensing period, in order to distinguish a sequence of signals for each of the pads.

In particular embodiments, a nucleic acid sequencing system can include (a) a detection apparatus having (i) an array of electrically responsive pads on a substrate surface; (ii) an array of pixels, wherein each pixel in the array has a detection zone on the surface that includes a subset of four of the pads; and (iii) an activation circuit to apply an electric field to the pads in the subset individually, wherein the activation circuit is configured to apply a different electric field at a first pad of the subset compared to the other pads of the subset; (b) a readout circuit to acquire signals from the array of pixels; (c) a control module that directs the readout circuit to acquire signals from each of the pixels during a sensing period and that directs the activation circuit to sequentially apply different electric fields at the four pads during the sensing period; and (c) a processing module that correlates (i) the signals acquired from the pixels during the sensing period and (ii) the sequential application of the different electric fields at the four pads during the sensing period, in order to distinguish a sequence of signals for each of the pads.

The disclosure further provides a method of detecting analytes. The method can include the steps of (a) providing a detection apparatus having an array of responsive pads and an array of pixels, wherein each pixel in the array has a detection zone that includes a subset of at least two of the responsive pads, wherein the two pads include different target analytes, respectively; (b) acquiring signals from each of the pixels while selectively applying a unique characteristic at a first of the two pads to preferentially produce signal from a first of the different target analytes compared to a second of the target analytes, thereby preferentially acquiring signals from the first of the target analytes compared to the second of the target analytes; and (c) acquiring signals from each of the pixels while selectively applying the unique characteristic at the second of the two pads to preferentially produce signal from the second of the different target analytes compared to the first of the target analytes, thereby preferentially acquiring signals from the second of the target analytes compared to the first of the target analytes.

In particular embodiments, a method of detecting analytes can include the steps of (a) providing a detection apparatus having an array of electrically responsive pads and an array of pixels, wherein each pixel in the array has a detection zone that includes a subset of at least two of the electrically responsive pads, wherein the two pads include different target analytes, respectively; (b) acquiring signals from each of the pixels while selectively applying an electric field at a first of the two pads to preferentially produce signal from a first of the different target analytes compared to a second of the target analytes, thereby preferentially acquiring signals from the first of the target analytes compared to the second of the target analytes; and (c) acquiring signals from each of the pixels while selectively applying an electric field at the second of the two pads to preferentially produce signal from the second of the different target analytes compared to the first of the target analytes, thereby preferentially acquiring signals from the second of the target analytes compared to the first of the target analytes.

The present disclosure also provides a detection apparatus that includes (a) an array of responsive pads on a substrate surface, wherein each responsive pad includes a nucleic acid feature of a plurality of nucleic acid features in the array, wherein a first subset of nucleic acid features in the plurality of nucleic acid features have a first universal sequence and different target sequences, wherein a second subset of nucleic acid features in the plurality of nucleic acid features have a second universal sequence and different target sequences, wherein the first universal sequence is different from the second universal sequence; (b) an array of pixels, wherein each pixel in the array has a detection zone on the surface that includes at least two nucleic acid features of the plurality of nucleic acid features, the at least two nucleic acid features including a nucleic acid from the first subset of nucleic acid features and a nucleic acid from the second subset of nucleic acid features; and (c) an activation module to alter a characteristic of a pad in the first subset and of a pad in the second subset, wherein the activation module is configured to apply a different characteristic at the pad in the first subset compared to the pad in the second subset, and wherein the activation module has a switch to selectively alter the characteristic at the pads in the first and second subsets. Optionally, the detection apparatus can be included in a nucleic acid sequencing system that also includes (I) a readout circuit to acquire signals from the array of pixels; (II) a control module that directs the readout circuit to acquire signals from each of the pixels during a sensing period and that optionally directs the activation circuit to sequentially actuate different responsive pads in each of the detection zones during the sensing period; and (III) a processing module that optionally correlates (i) the signals acquired from the pixels during the sensing period and (ii) the sequential actuation of the different responsive pads during the sensing period, in order to distinguish a sequence of signals for each of the pads.

Also provided is a method of detecting target nucleic acids, including the steps of (a) providing a substrate comprising an array of pads, the array of pads including a first subset of the pads and a second subset of the pads; (b) delivering a first solution to the substrate, wherein the first solution includes a first plurality of different target nucleic acids that selectively attach to the first subset of pads compared to the second subset of pads; (c) delivering a second solution to the substrate, wherein the second solution includes a second plurality of different target nucleic acids that selectively attach to the second subset of pads compared to the first subset of pads; and (d) detecting the substrate using an apparatus having an array of pixels, wherein each pixel in the array has a detection zone that includes (i) at least one of the target nucleic acids that is attached to a pad of the first subset of pads, and (ii) at least one of the target nucleic acids that is attached to a pad of the second subset of pads.

In some embodiments, a method of detecting nucleic acids can include the steps of (a) providing a substrate comprising an array of pads, the array of pads including a first subset of the pads and a second subset of the pads; (b) contacting a solution of adapter nucleic acids with the substrate while selectively actuating one or both of the subsets of responsive pads, wherein the adapter nucleic acids attach to responsive pads of the one or both subsets that are selectively actuated; (c) contacting a first solution with the substrate, wherein the first plurality of different target nucleic acids attach to responsive pads of the first subset; (d) contacting a second solution with the substrate, wherein the second plurality of different target nucleic acids attach to responsive pads of the second subset, wherein the responsive pads of one or both of the first and second subset are attached to the adapter nucleic acids; and (e) detecting the substrate using an apparatus having an array of pixels, wherein each pixel in the array has a detection zone that includes (i) at least one of the target nucleic acids that is attached to a pad of the first subset of pads, and (ii) at least one of the target nucleic acids that is attached to a pad of the second subset of pads.

DETAILED DESCRIPTION

Figure 1:
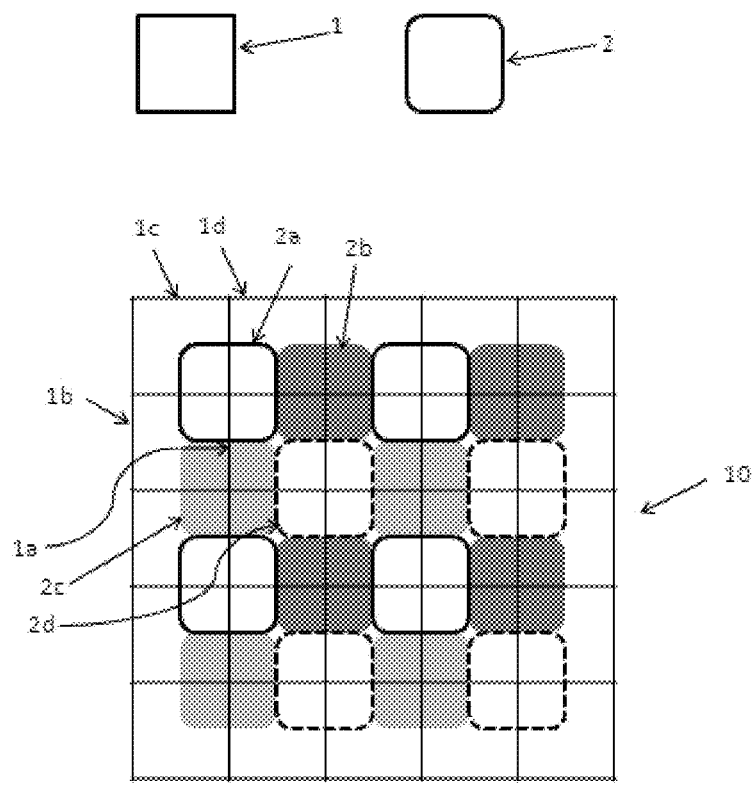
FIG. 1 shows a diagrammatic view of a detection apparatus having an array of pixels and an array of electrically responsive pads.

This disclosure provides apparatus and methods for super resolution imaging. The resolution of standard imaging techniques is constrained by the number of pixels available in the detection device, among other things. Standard imaging techniques provide, at best, a single pixel for detection of each feature in an object. Often several pixels must be used to collect signal from each feature in order to obtain sufficient signal to noise. In contrast, the super resolution imaging methods provided by the current disclosure break the one-pixel-per-feature barrier and allow several features to be distinguished by a single pixel. This leads to advantages of reducing the optics hardware required to detect an object of a given size and complexity. This can also increase the resolution of a detection apparatus beyond the resolution of the optics module being used. Thus, costs incurred in manufacturing and using optics hardware can be reduced substantially.

In embodiments set forth herein, two features can be resolved with a single pixel by differential treatment of the features to render one of the features detectable in a first state and the other feature detectable in another state. By extension, several features can be resolved by a single pixel by sequentially actuating individual features to a detectable state while the other features are in an undetectable state.

A particularly useful application of the present apparatus and methods is the detection of analytes, such as nucleic acids, on solid supports, such as arrays of features to which the analytes are attached. In particular embodiments, the solid support has several responsive pads that are in the detection zone of a particular pixel and each pad has a different target analyte attached. The pads can be switchable between different states such that a single pad is in a first state that produces signal from the respective analyte; meanwhile the other pads are in a different state such that the analytes at these other pads do not produce a detectable signal. For example, the single pad may have an electric field that attracts a detectable label (e.g. a fluorophore), removes a detection inhibitor (e.g. a fluorescence quencher) or induces electrochemical luminescence. By sequentially switching the states (e.g. strength, polarity or presence of an electric field) at the pads that are in the detection zone, the different analytes can be individually induced to produce signal. By detecting the pads in the different states the pixel can achieve super resolution detection of several different analytes in its detection zone. An accounting of which pads were actuated at different times during acquisition of signal by the pixel will allow the respective analytes to be distinguished.

Alternatively or additionally, to differential treatment of two features during detection events, two features can be distinguished by one pixel based on physical or chemical differences that were imparted to the features prior to the detection events. Thus, the two features need not be switched between different states during or between detection steps. For example, each of the two different target nucleic acid features within the detection zone of the same pixel can have different priming sequences such that they can be distinguished by hybridizing different primers to each feature and/or extending different primers at each feature. The hybridization and/or extension can occur at the respective features at different times. In multiplex formats, the priming sites can be universal sequences such that a first subset of features in the array share a first universal priming site sequence and a second subset of features in the array share a second universal priming site sequence. In this multiplex format, individual pixels can have a detection zone that includes a feature from each subset. Thus each pixel can be capable of super resolution detection based on differential primer hybridization. For example, different primers can be delivered sequentially for separate detection of features at different times.

By way of further illustrative example, two pads that are in the detection zone of the same pixel can differentially capture target nucleic acids. Differential capture can be facilitated by use of specific capture probes that are attached at respective pads and that are selective for different target nucleic acids. Nanofabrication methods, such as those used in the manufacture of nucleic acid microarrays, can be used to place different capture probes at separate features within the detection zone of the same pixel. Alternatively, the same capture probes can be present at both pads in the detection zone, but the pads can be differentially activated in the presence of different adapter nucleic acids such that the capture probes on the two different pads hybridize to different adapter nucleic acids. The different adapter nucleic acids can include a common sequence that is complementary to the capture probes and different selective capture sequences that are complementary to different target nucleic acids. As such, these adapters can convert a universal surface to one that is capable of selective target nucleic acid capture.

Similarly, different nucleic acids present on two pads can serve as hybridization sites for different amplification primers or different detection primers. Different amplification primers can be used for differential amplification of target nucleic acids before or during a detection event. In this example a first amplification primer can amplify a subset of target nucleic acid templates that have a first universal priming site that is complementary to the first amplification primer. A second amplification primer can amplify a subset of target nucleic acid templates that have a second universal priming site that is complementary to the second amplification primer. The different amplification primers can be delivered to an array of pads at different times to create colonies at a first subset of the pads for a first sensing period followed by creation of colonies at a second subset of pads for a second detection event. Different extension primers can be used for differential detection of target nucleic acids for example in techniques such as sequencing-by-synthesis, sequencing-by-ligation, single base extension, oligonucleotide ligation, allele specific primer extension or the like. In this example a first extension primer can be used to detect a subset of target nucleic acid templates that have a first universal priming site that is complementary to the first extension primer and a second extension primer can detect a subset of target nucleic acid templates that have a second universal priming site that is complementary to the second extension primer.

As exemplified in further detail below, super resolution imaging can be achieved using electrically responsive pads, for example, to achieve electric field assisted transport of charged species to or from the pad. Other types of responsive pads can be used similarly in an apparatus or method set forth herein. For example, a responsive pad can alter other forces to create non-diffusive forces on target analytes, probes or other materials of interest (whether charged or not). Non-diffusive forces can be provided by an external source such as those that produce an electrical or magnetic field, or an agent that imposes molecular crowding or chemical gradients within a reaction volume. For example, magnetic or optical forces can be used to increase the local concentration of desired materials at a pad in an array of pads or to decrease the local concentration of the materials at a particular pad. In such cases, the materials can include a magnetic tag or optical tag that can be manipulated by such forces. Other useful responsive pads can alter detection properties of an analyte at the pad, for example, by inducing chemical changes at or near the pad that activate, inhibit, destroy or create a detectable label. Such pads can be used to replace electrically responsive pads exemplified in several embodiments of the apparatus and methods set forth herein.

Particular embodiments of the super resolution apparatus and methods set forth herein provide the advantage of reducing the number of different excitation lines and/or fluorophore labels required to observe an analyte. In many fluorescent detection systems, analytes are labeled with multiple different fluorophore labels, respectively, and the labels are distinguished by use of multiple different excitation wavelengths. Using the super resolution apparatus and methods of the present disclosure, responsive pads (e.g. electrically responsive pads) can remove the necessity for multiple fluorophores and multiple excitation lines. For example, instead of using two different fluorophores and two different lasers to distinguish two analytes in a detection area, two responsive pads can occur in the detection area. The pads, although having different analytes, can be labeled with the same fluorophore and excited with the same excitation laser. However, it will be understood that in some embodiments multiple excitation lines can be used in combination with super resolution to further expand the number of different analytes detected by a given pixel. More specifically, multiple features in the detection zone of a pixel can be individually actuated to produce or inhibit signals, and features that are active can be excited sequentially with different radiation lines. As such, a pixel can distinguish a number of analytes that is equivalent to the mathematical product of the number of responsive pads in the detection zone of the pixel multiplied by the number of excitation lines that produce emission at each of the pads.

An alternative to actuated pads is to use pads that are manufactured to have different physical or chemical properties. Taking as an example, nucleic acid-based techniques, two pads that are, or will be, present in the detection zone of the same pixel can be nanofabricated to include different capture nucleic acids. A first feature can have a first capture sequence and a second feature can have a second capture sequence. In array formats, a first subset of features can have capture probes with a first universal sequence and a second subset of features can have capture probes with a second universal sequence.

The present disclosure provides a detection apparatus that includes (a) an array of electrically responsive pads on a substrate surface; (b) an array of pixels, wherein each pixel in the array has a detection zone on the surface that includes a subset of at least two of the electrically responsive pads; and (c) an activation circuit to apply an electric field at a first pad in the subset and a second pad in the subset, wherein the activation circuit is configured to apply a different electric field at the first pad compared to the second pad, and wherein the activation circuit has a switch to selectively alter the electric field at the first pad compared to the second pad.

As used herein, the term "electrically responsive pad" means an area on the surface of a substrate that produces an electric field. The area on the surface can form an interface between the substrate and a fluid that is in contact with the substrate. Thus, the electric field can attract electrically charged species from the fluid to the pad or the field can repel electrically charged species from the pad. The direction of active transport to or from the pad will depend upon the charge of the species in solution and the charge of the field at or near the pad. Specifically, positively charged species, such as positively charged fluorophores or other optical labels, receptors, ligands, quenchers, labeled probes or the like, can be attracted to the pad by inducing a negative charge at or near the pad. Conversely, negatively charged species, such as nucleic acids, nucleotides, or negatively charged fluorophores, optical labels, receptors, ligands, quenchers, labeled probes or the like, can be attracted to the pad by inducing a positive charge at or near the pad.

As used herein, the term "electric field," when used in reference to an electrically responsive pad, means the effect produced by the existence of an electric charge on the pad or in the volume of a medium that surrounds the pad. A charge placed in the volume of a medium has a force exerted on it. Electric fields are created by differences in voltage: the higher the voltage, the stronger will be the resultant field. In contrast, magnetic fields are created when electric current flows: the greater the current, the stronger the magnetic field. An electric field will exist whether or not current is flowing. Electric fields can be measured in Volts per meter (V/m) or similar units. Electric field strength of about 5 V/cm or higher, up to practical limits of Joule heating and dielectric breakdown limits, are particularly useful to cause movement of charged particles and species in the present methods and apparatus. In particular embodiments, the maximum upper value for the field strength is about 1000 V/cm.

Electrical potential greater than the redox potential of water, roughly 1.23 V, will cause electrolysis of water. In some embodiments, such as those using aqueous fluids, the applied voltages can be in the range of −1 V to +1 V. In some embodiments, it may be beneficial to employ a common ground counter electrode separating the pads to minimize diffusion of labels, target analytes or other substances from one pad to another.

Particular embodiments use an AC electric field with DC bias to attract or repel charged species. Exemplary configurations for applying an AC electric field with DC bias are set forth in U.S. Pat. No. 8,277,628, which is incorporated herein by reference.

As used herein, the term "different electric field," when used with respect to a reference electric field, includes, for example, a field having opposite charge compared to the reference field, no charge compared to the reference field, greater or lesser charge compared to the reference field, a DC induced charge compare to an AC induced charge at the reference field, or an AC induced charge compared to a DC induced charge at the reference field.

The conductive surfaces of a pad can be metallic (e.g. gold, titanium, indium tin oxide) or semiconducting in nature. In some embodiments, it may be desirable to use an electrical conductor that is transparent to radiation used in an optical detection step. Examples of optically transparent electrode materials include, but are not limited to metal oxides such as indium tin oxide, antimony doped tin oxide, and cadmium tin oxide. This is particularly useful in configurations where the pad occurs between a target analyte and a pixel that will detect the analyte and/or when the pad occurs between a target analyte and an excitation source used in a fluorescence technique.

In particular embodiments, electrically responsive pads can be electrically coupled to a power source to produce an electric charge that attracts target nucleic acids or other substances. In one configuration, a positive charge at the pad can attract nucleic acids via the negatively charged sugar-phosphate backbone. Exemplary methods and apparatus for using e-field assist to attract nucleic acids or other substances to sites of an array are described in U.S. Pat. No. 8,277,628, which is incorporated herein by reference. Alternatively, pads of an array can be electrically coupled to a power source to produce an electric charge that inhibits binding of or removes target nucleic acids or other substances from the pads. In one configuration, a negative charge at the pads can repel nucleic acids via the negatively charged sugar-phosphate backbone.

A low conductivity and low ionic buffers, such as 10-100 mM histidine, can be used to promote electrophoretic transport of a label, target analyte or other substance to or from an electrically responsive pad. A low ionic strength buffer also provides a benefit of increasing the Debye length, effectively increasing the spatial extent of the electric field in the solution above the activated pad.

Although several methods and apparatus of the present disclosure are exemplified with regard to electrically responsive pads, it will be understood that other responsive pads can be used in place of these. As used herein, the term "responsive pad" means an area on the surface of a substrate that can be physically or chemically manipulated to alter a surface characteristic. The area on the surface can form an interface between the substrate and a fluid that is in contact with the substrate. A change in a surface characteristic of the pad can induce a change in the fluid that contacts the pad. Exemplary characteristic that can be altered include, but are not limited to, electric field, electric current, temperature, magnetic field, or a chemical property such as pH, redox potential, hydrophobicity, hydrophilicity or chemical reactivity. A characteristic of a responsive pad can be altered to change the direction of transport of a material or substance to or from the pad. A characteristic of a responsive pad can also be altered to change the chemical composition or structural integrity of a material or substance at the pad.

As used herein, the term "electrowetting control pad" refers to a pad or area comprising an electrode covered by a hydrophobic layer. The hydrophobic layer becomes hydrophilic upon activation of the electrowetting control pad. The size of the electrowetting control pad is generally approximately equivalent to the size of the electrode. In particular embodiments, two or more electrodes can be configured to be in the detection zone of the same pixel. More particularly, features located on two or more different electrowetting control pads can be located within the detection zone of the same pixel.

As used herein, the term "transport" refers to movement of a molecule through a fluid. The term can include passive transport such as movement of molecules along their concentration gradient (e.g. passive diffusion). The term can also include active transport whereby molecules can move against their concentration gradient or at an increased rate of passage along their concentration gradient. Thus, transport can include applying energy to move one or more molecule in a desired direction or to a desired location such as a pad in an array of pads. Active transport can be provided by an external source such as those that produce electric or magnetic fields, or an agent that imposes molecular crowding or chemical gradients within a reaction volume. For example, magnetic or optical forces can be used to increase the local concentration of amplification reagents. In such cases, one or more amplification reagents can include a magnetic tag or optical tag that can be manipulated by such forces.

An array of pixels can be configured such that each pixel in the array has a detection zone that includes a subset of at least two pads or other features to be detected. As used herein, the term "detection zone," when used in reference to a pixel, means a location that is simultaneously observed by the pixel. The location can be, for example, a volume of space or area on a surface. For example, a detection zone can include an area on the surface of an array of pads that includes a subset of the pads. For example, the detection zone of an individual pixel can include at least 2, 3, 4, 5, 10 or more pads or features. The number of pads or features in a detection zone can be selected to suit the size of the pixel, the size of the detection zone for the pixel (for example, as influenced by optics between the pixel and the features or pads observed), the size of the features or pads, or the size of any analytes to be detected by the pixel. In particular embodiments, a maximum number of pads or features in a detection area can be 10, 5, 4, 3 or 2.

As used herein, the term "each," when used in reference to a collection of items, is intended to identify an individual item in the collection but does not necessarily refer to every item in the collection. Exceptions can occur if explicit disclosure or context clearly dictates otherwise. Thus, reference to each pixel in an array having a detection zone that includes a subset of at least two pads, means that at least one pixel in the array has a detection zone that includes the subset of pads. Although all of the pixels in the array may have a similarly configured detection zone, not all of the pixels in the array need to be so configured. Rather some pixels may not have any pads in their respective detection zone or some pixels may have only one pad in the respective detection zone.

A diagrammatic representation of a relationship between an array of pixel detection zones and an array of responsive pads that provides super resolution imaging is shown in FIG. 1. Detection apparatus 10 has a 5×5 array of pixel detection zones 1 and a 4×4 array of responsive pads 2. The arrays are offset such that each pixel detection zone 1 includes four different pads 2. For example pixel detection zone 1a includes pads 2a, 2b, 2c and 2d. In this exemplary configuration, each pad 2 occurs in the detection zone of four different pixels 1. For example, pad 2a is in the detection zone of pixels 1a, 1b, 1c and 1d. In the exemplified configuration of FIG. 1, each detection zone is square and each pad occurs in a corner of four of the detection zones. Furthermore each pad is exemplified as being square and each detection zone includes a corner of four of the pads. As used herein, the term "in a corner" means at or near the intersection of two vertices. For example, an object that occurs in all or part of one quadrant of a square area can be considered to be in the corner of the square area.

In the exemplary configuration of FIG. 1, the array of pads has roughly the same pitch (center to center spacing for the pads) as the pitch for the array of pixels. Also the pads have an area that is roughly equivalent to the area of each pixel's detection zone (although the areas for any given pad and detection zone only partially overlap due to the offset between the two arrays). Also, the pads are adjacent to each other and the pixel detection zones are adjacent to each other. Thus, the pads and pixels have the same spacing. This configuration is exemplary as the pitch, areas and spacing can differ for the two arrays.

In some embodiments, the pads can have a pitch that is less than the pitch for the detection zones. This can allow greater than four pads per detection zone in the rectilinear configuration such as the one exemplified in FIG. 1. Depending upon the desired use, the array of pads on a surface can have a pitch that is no greater than the pitch of the detection areas, no greater than half the pitch of the detection areas, no greater than a quarter of the pitch of the detection areas or no greater than a tenth of the pitch of the detection areas, or smaller pitch.

The areas for individual pads can be substantially smaller than the area of each detection zone. In particular embodiments this can allow each detection zone to include several pads while each pad is present in only a single detection zone (in contrast to the example of FIG. 1 where each pad is present in four detection zones). The area for individual pads on a surface can be at most the same as the detection area, at most 75% of the detection area, at most 50% of the detection area, at most 25% of the detection area or at most 10% of the detection area or smaller.

The pads are exemplified as being juxtaposed to each other and pixel detection zones are also exemplified as being juxtaposed to each other in FIG. 1. In alternative embodiments, spacing can occur between pads or between pixel detection zones. The spacing for one of the arrays can be equivalent or different compared to the other array. For example, the spacing between the pads on a surface can be greater or smaller than the spacing between the pixel detection areas on the surface.

Although detection areas and pads are exemplified above as being square, it will be understood that reactive pads on a surface and/or pixel detection areas on the surface can have other shapes including, but not limited to, rectangular, circular, oval, hexagonal, triangular, polygonal or the like. A particularly illustrative example is a hexagonally packed array. Hexagonal packing is a particularly useful configuration for close packing of round pads or round detection areas. In an exemplary hexagonal arrangement, each pixel in an array can have a detection area that is round and includes a subset of seven responsive pads on the surface of a substrate. Furthermore in this packing, each pad can be included in the detection areas for three of the pixels. Thus each detection area can be considered as approximating a hexagon and each pad can be considered to cross into three detection zones at a corner of each hexagon. Alternatively, each pad can have an area that is round and can be included in seven detection areas on the surface of a substrate. Furthermore in this packing, each pixel in the array can have a detection area on the surface that includes three of the pads. Thus, each pad can be considered as approximating a hexagon and each detection area can be considered to cross into three detection zones at a corner of each hexagon.

An apparatus or system of the present disclosure can include an array of pixels that are in a complementary metal oxide semiconductor (CMOS) sensor, charge coupled device (CCD) sensor or other digital cameras. In some embodiments the pixels are used to detect chemiluminescence, electrochemical luminescence or other optical signals that do not require excitatory radiation. However, many embodiments utilize fluorescence based detection. In these cases, an apparatus or system of this disclosure can include an optical excitation assembly. Radiation can be provided from a laser, light emitting diode (LED), or other appropriate radiation source. Furthermore the radiation can be conditioned by optics to reflect, filter, shape, direct or otherwise manipulate the excitation radiation.

Embodiments described herein may utilize a step-and-shoot procedure in which different portions of an array of pads are individually detected or imaged between (or after) relative movements of the detector and sample. For example, each area of the array can be excited with a laser or other appropriate radiation source and emission can be detected using an array of pixels configured for super resolution imaging. Examples of step-and-shoot optical components that can be modified for super resolution imaging in accordance with the present disclosure are set forth in US Pat. App. Pub. No. 2012/0270305 A1, which is incorporated herein by reference. Embodiments described herein may utilize a scanning procedure in which different portions of an array of pads are detected or imaged during movement between the pads and optical components. In some embodiments, the imaging assembly includes a scanning time-delay integration (TDI) system. Furthermore, the imaging sessions may include line-scanning one or more samples such that a linear focal region of light is scanned across the array of pads. Some methods of line-scanning that can be modified for super resolution imaging in accordance with the present disclosure are described, for example, in U.S. Pat. No. 7,329,860 and U.S. Pat. Pub. No. 2009/0272914, each of which is incorporated herein by reference. Scanning may also include moving a point focal region of light in a raster pattern across the array of pads. Whether using step-and-shoot, scanning, static image collection or other configurations, embodiments can be configured for epi-fluorescent imaging or total-internal-reflectance-fluorescence (TIRF) imaging. Exemplary optical components and arrangements that can be modified for super resolution imaging in this regard are set forth in U.S. patent application Ser. No. 13/766,413; US Pat. App. Pub. Nos. 2010/0111768 A1 and 2012/0270305 A1; and U.S. Pat. Nos. 7,329,860 and 8,241,573, each of which is incorporated herein by reference.

Certain embodiments include objective lenses having high numerical aperture (NA) values. Exemplary high NA ranges for which embodiments may be particularly useful include NA values of at least about 0.6. For example, the NA may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. However, other embodiments may have lower NA values than the examples listed above. Image data obtained by the optical assembly may have a resolution that is between 0.1 and 50 microns or, more particularly, between 0.1 and 10 microns. Optical assemblies may have a resolution that is sufficient to individually resolve the features or sites that are separated by a distance of less than 15 μm, 10 μm, 5 μm, 2 μm, 1 μm, 0.5 μm, or less.

In general, the NA value of an objective lens is a measure of the breadth of angles for which the objective lens may receive light. The higher the NA value, the more light that may be collected by the objective lens for a given fixed magnification. This is because the collection efficiency and the resolution increase. As a result, multiple pads or features may be distinguished more readily when using objectives lenses with higher NA values. Therefore, in general, a higher NA value for the objective lens may be beneficial for imaging.

The size of the pads (or target analyte features) and/or spacing between the pads (or target analyte features) can vary such that arrays can be high density, medium density or low density. High density arrays are characterized as having pads (or features) separated by less than about 15 μm. Medium density arrays have pads (or features) separated by about 15 to 30 μm, while low density arrays have pads (or features) separated by greater than 30 μm. An array useful in some embodiments can have pads (or features) that are separated by less than 100 μm, 50 μm, 10 μm, 5 μm, 1 μm, or 0.5 μm. An apparatus or method of the present disclosure can be used to image an array of pads or features at a resolution sufficient to distinguish pads or features at the above densities or density ranges. In particular embodiments the size of the responsive pads can be smaller than the resolution limit of the detector component that is used. In this way, the super resolution methods and apparatus of the present disclosure can distinguish target analyte features at a resolution beyond the limits of the detector component.

Figure 2:
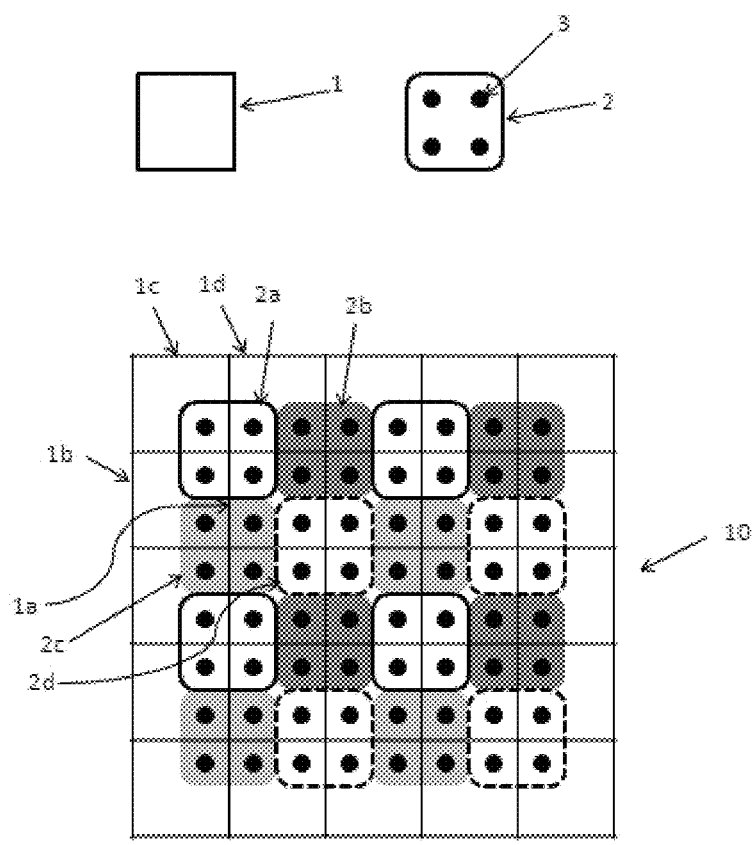
FIG. 2 shows a diagrammatic view of a detection apparatus having an array of pixels and an array of electrically responsive pads, wherein the pads each have multiple target analyte features.

FIG. 2 shows a diagrammatic representation of an array of pixel detection zones 1, an array of responsive pads 2 and an array of target analyte features 3 that are configured to provide super resolution imaging of the features 3. Each target analyte feature 3 is shown as being in the corner of a pad 2 that occurs in a detection zone of a pixel 1. For example pixel detection zone 1a includes a target analyte feature 3 that is present on each of pads 2a, 2b, 2c and 2d, respectively. In this exemplary configuration (i) each target analyte feature occurs in a single detection zone, (ii) each detection zone includes four different target analyte features and each target analyte feature is present on a different responsive pad than the other target analyte features in the respective detection zone. Thus, each pixel can distinguish the four target analytes based on differential actuation of the four pads, respectively.

In an alternative embodiment to that exemplified in FIG. 2, a target analyte can occur in multiple detection zones. For example, one can envision a situation where the four target analyte features 3 on pad 2a are replaced with a single feature that occupies the entire surface area of pad 2a. As such the target analyte feature will occur in the four detection zones 1a, 1b, 1c and 1d. In this situation activation of signal at pad 2a will result in detection by all four of the pixels. However, in this configuration each pixel will still include four pads in its detection zone.

A detection zone can include multiple target analyte features, each on a separate responsive pad from others in the detection zone. For example, the detection zone of an individual pixel can include at least 2, 3, 4, 5, 10 or more target analyte features, each on separate responsive pads. The number of target analyte features in a detection zone can be selected to suit the size of the pixel, the size of the detection zone for the pixel (for example, as influenced by optics between the pixel and the features or pads observed), the size of the pads and the size of the target analyte features. In particular embodiments, a maximum number of target analyte features in a detection area can be 10, 5, 4, 3 or 2.

Any of a variety of target analytes that are to be detected, characterized, or identified can be used in an apparatus, system or method set forth herein. Exemplary analytes include, but are not limited to, nucleic acids (e.g. DNA, RNA or analogs thereof), proteins, polysaccharides, antibodies, epitopes, receptors, ligands, enzymes (e.g. kinases, phosphatases or polymerases), small molecule drug candidates, cells, viruses, organisms, or the like. An array of pads can include multiple different species from a library of analytes. For example, the species can be different antibodies from an antibody library, nucleic acids having different sequences from a library of nucleic acids, proteins having different structure and/or function from a library of proteins, drug candidates from a combinatorial library of small molecules, cells from a culture, tissue or organism, etc.

In some embodiments, analytes can be distributed on pads such that they are individually resolvable. For example, a single molecule of each analyte can be present at each pad. Alternatively, analytes can be present as colonies or populations such that individual molecules or cells are not necessarily resolved. The colonies or populations can be homogenous with respect to containing only a single species of analyte (albeit in multiple copies). Taking nucleic acids as an example, each pad in an array of pads can include a colony or population of nucleic acids and every nucleic acid in the colony or population can have the same nucleotide sequence (either single stranded or double stranded). Colonies of nucleic acids can also be referred to as 'nucleic acid clusters'. Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure. Thus, a responsive pad can contain multiple copies of a single species of an analyte. Alternatively, a colony or population of analytes that are at a pad can include two or more different species. For example, one or more pads in an array of pads can each contain a mixed colony having two or more different nucleic acid species (i.e. nucleic acid molecules with different sequences). The two or more nucleic acid species in a mixed colony can be present in non-negligible amounts, for example, allowing more than one nucleic acid to be detected in the mixed colony.

As set forth above for target analyte features in general, each pad in an array of pads can include a plurality of nucleic acid clusters and each cluster can occur in the detection zone for a single pixel. Alternatively, each cluster can occur in the detection zones for several pixels. For example, each pad can include only a single nucleic acid cluster and the cluster can be included in the detection zones for at least two pixels.

In some embodiments, at least two nucleic acid clusters are included in the detection zone for a single pixel. Each of the clusters can be homogenous with respect to the nucleotide sequence present and the two clusters can have different nucleotide sequences compared to each other. The clusters can be labeled, for example, by a labeled nucleotide that has been incorporated in the course of a sequencing-by-synthesis (SBS) technique. Other labels are possible too such as those set forth elsewhere herein. The two clusters can have the same label as each other or a different label can be present at each of the two clusters. For example, in an SBS technique the identity of the labels will depend upon the sequences of the two clusters at the position of nucleotide incorporation. This example can be extended to formats where 3 or 4 or more nucleic acid clusters are included in the detection zone for a single pixel. Accordingly, multiple clusters can have different nucleotide sequences from each other and can be labeled with probes that are the same or different.

As used herein, the term "different", when used in reference to nucleic acids, means that the nucleic acids have nucleotide sequences that are not the same as each other. Two or more different nucleic acids can have nucleotide sequences that are different along their entire length. Alternatively, two or more different nucleic acids can have nucleotide sequences that are different along a substantial portion of their length. For example, two or more different nucleic acids can have target nucleotide sequence portions that are different from each other while also having a universal sequence region that is the same for both (or all).

In particular embodiments, two clusters that are present in the detection zone for the same pixel can be distinguished from each other due to the presence of different priming sequences. A first of the two clusters can be selectively hybridized to a first primer that has specificity for a first priming sequence present the first cluster compared to a second priming sequence that is present on the second cluster. The first cluster can be detected or sequenced based on hybridization of the first primer, for example, if the first primer has a detectable label or if the first primer undergoes a reaction, such as nucleotide extension, oligonucleotide ligation, sequencing by synthesis or other technique, that recruits label(s) to the cluster. In turn, the second cluster can be detected based on specificity for a second primer to the second priming sequence compared to the first priming sequence. The second cluster can be selectively detected or sequenced using the techniques exemplified above for the first cluster.

Analytes can be attached to a responsive pad. The attachment can be covalent or non-covalent. In some embodiments, the attachment can be mediated by a gel material. The analytes can be nucleic acids that are attached to a gel material. Exemplary methods and reactants for attaching nucleic acids to gels are described, for example, in US Pat. App. Pub. No. 2011/0059865 A1, or U.S. patent application Ser. No. 13/784,368, each of which is incorporated herein by reference. Nucleic acids can be attached to the gel or to the surface of a pad via their 3' oxygen, 5' oxygen, or at other locations along their length such as via a base moiety of the 3' terminal nucleotide, a base moiety of the 5' nucleotide, and/or one or more base moieties elsewhere in the molecule. Non-covalent modes of attachment include, for example, ionic interactions between nucleic acid and a surface (or gel), entrapment of nucleic acid within pores of a gel, protein-protein interactions, binding between receptors and ligands and/or nucleic acid, and other known modes.

An apparatus of the present disclosure can include a flow cell. Exemplary flow cells, methods for their manufacture and methods for their use are described in US Pat. App. Publ. Nos. 2010/0111768 A1 or 2012-0270305 A1; or WO 05/065814, each of which is incorporated herein by reference. Flow cells provide a convenient format for housing an array of responsive pads and that is subjected to a sequencing-by-synthesis (SB S) reaction or other technique that involves repeated delivery of reagents in cycles (e.g. synthesis techniques or detection techniques having repetitive or cyclic steps).

Any of a variety of labels or moieties can be present at a responsive pad. Exemplary labels and moieties include, but are not limited to fluorophores, chromophores, chemiluminescent species, electrochemical luminescence species, fluorescence quenchers, donors and/or acceptors for fluorescence resonance energy transfer (FRET), nanocrystals and the like. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, phycoerythin, and others known in the art such as those described in Haugland, Molecular Probes Handbook, (Eugene, Oreg.) 6th Edition; The Synthegen catalog (Houston, Tex.), Lakowicz, *Principles of Fluorescence Spectroscopy*, $2^{nd}$ Ed., Plenum Press New York (1999), or WO 98/59066, each of which is hereby incorporated by reference. Exemplary quenchers include, but are not limited to, DACYL(4-(4'-dimethylaminophenylazo)benzoic acid), Black Hole Quenchers (Biosearch Technologies, Novato, Calif.), Qxl quenchers (Anaspec, Freemont, Calif.), Iowa black quenchers, DABCYL, BHQ1, BHQ2, QSY7, QSY9, QSY21, QSY35, BHQO, BHQ1, BHQ2, QXL680, ATTO540Q, ATTO580Q, ATTO612Q, DYQ660, DYQ661 and IR Dye QC-1 quenchers. Chemiluminescent species include, for example, luminal, reagents used for detection in pyrosequencing, aequorin and other species known in the art. Exemplary electrochemical luminescence species include, but are not limited to $Ru(bpy_3)^{2+}$, Bodipy dyes, luminal derivatives, acridine esters and others known in the art.

A label or moiety can be selected to suit a particular application of an apparatus, system or method set forth herein. For example, the label or moiety can be associated with a target analyte that is present at the pad and detected using a technique set forth below. The label or moiety can be in a detectable state or a non-detectable state, for example, as influenced by a characteristic of a responsive pad at which the label or moiety is present. Thus, a probe or moiety can be located in a detection zone of a pixel and the probe or moiety can optionally be in a state that produces a signal that is detected by the pixel.

In particular embodiments, target analytes include fluorescent moieties and the pixels are configured to detect emission from the fluorescent moieties. An apparatus that includes the fluorescent moieties can further include an excitation assembly as set forth herein or otherwise known in the art. An apparatus with an excitation assembly is also useful when using fluorescence quenchers, donors and/or acceptors for fluorescence resonance energy transfer (FRET) or nanocrystals. Responsive pads where target analytes occur can be selectively placed in a state to preferentially produce fluorescent signals. For example, a responsive pad can be electrically activated to create an electric field that selectively attracts a fluorescent label, donor, acceptor or nanocrystal to the pad, thereby producing a fluorescent signal at the pad. Alternatively, a responsive pad can be electrically activated to create an electric field that selectively repels or degrades a fluorescence quencher, thereby preferentially producing a fluorescent signal from a label or moiety that was previously quenched. In yet another example, a responsive pad can be electrically activated to create an electric field that selectively repels or degrades a fluorescent label, donor, acceptor or nanocrystal, thereby inhibiting fluorescent signals from the pad. Such inhibition can also result by electrically activating a pad to create an electric field that selectively attracts a fluorescence quencher. It is also possible to place a responsive pad in a state (e.g. a neutral state) where the above reagents are allowed to diffuse away. Differential activation of responsive pads in such ways can be used to achieve super resolution detection of fluorescent target analytes present at multiple responsive pads in the detection zone of a single pixel.

Similarly, responsive pads having chemiluminescent moieties or electrochemical luminescence moieties can be placed in different states to achieve super resolution imaging. An apparatus used for chemiluminescent or electrochemical luminescence detection can be configured similar to that exemplified above for use of fluorescent moieties, except that an excitation assembly is not necessary. Rather, signal generation can be achieved by activating a responsive pad to create an electric field that selectively attracts a chemical capable of generating chemiluminescence, and signal can be inhibited by activating the pad to create an electric field that repels or degrades the chemical. Electrochemical luminescence signal generation can be achieved by activating a responsive pad to carry out a redox reaction that produces the signal, and switching the pad can inhibit signal due to the pad being in a state where the redox reaction does not occur. Conversely, a responsive pad can be actuated to carry out a redox reaction that inhibits signal and a switch can alter the pad to a state where the redox reaction does not occur so that signal can be generated.

Several embodiments set forth herein illustrate differentiation of two or more features in the detection zone of the same pixel using differential activation of responsive pads to which the features are attached (or otherwise functionally associated) during a detection step, between detection steps or after a detection step. Alternatively or additionally, two features that are present in the detection zone of the same pixel can be distinguished based on a chemical or physical distinction that is introduced prior to a particular detection step. Taking as an example nucleic acid features, two or more pads can be differentially actuated during one or more of target nucleic acid capture, target nucleic acid amplification or hybridization of a primer used for detection of the nucleic acids. For example, a first library of target nucleic acids that includes members having a first universal priming sequence can be captured on a first subset of responsive pads and/or amplified on the first subset of pads. A second library of target nucleic acids that includes members having a second universal priming sequence can be captured on a second subset of responsive pads and/or amplified on the second subset of pads. The pixels and features can be arranged such that a feature from the first subset and a feature from the second subset are both located in the detection zone of a particular pixel. These two features can be distinguished without necessarily applying differential actuation during a detection step, after a detection step or between detection steps. Rather, the features can be distinguished based on nucleic acid hybridization specificity whereby a first primer selectively hybridizes to the first universal priming sequence and a second primer selectively hybridizes to the second universal priming sequence.

In the above examples, it will be understood that changing the state of responsive pads relative to each other can result in filling a pad to capacity with a particular reagent (e.g. label or probe), removing all of a particular reagent from a pad, degrading all of a particular reagent at a pad or modifying all of a particular reagent at a pad. However, in most embodiments it will be sufficient and in some cases even desirable that differential actuation of responsive pads results in higher relative concentrations of a particular reagent at one pad compared to another. For example an attractive electric field applied at a first pad can create a relatively higher concentration of a fluorophores, chromophores, chemiluminescent species, electrochemical luminescence species, fluorescence quenchers, donors and/or acceptors for fluorescence resonance energy transfer (FRET), nanocrystals or other reagents at the first pad compared to at a second pad where the field is not applied or where a different field is applied. Similarly, a repellant or destructive field applied at a first pad can create a relatively lower concentration of these or other reagents at the first pad compared to at a second pad where the field is not applied or where a different field is applied.

Figure 3:
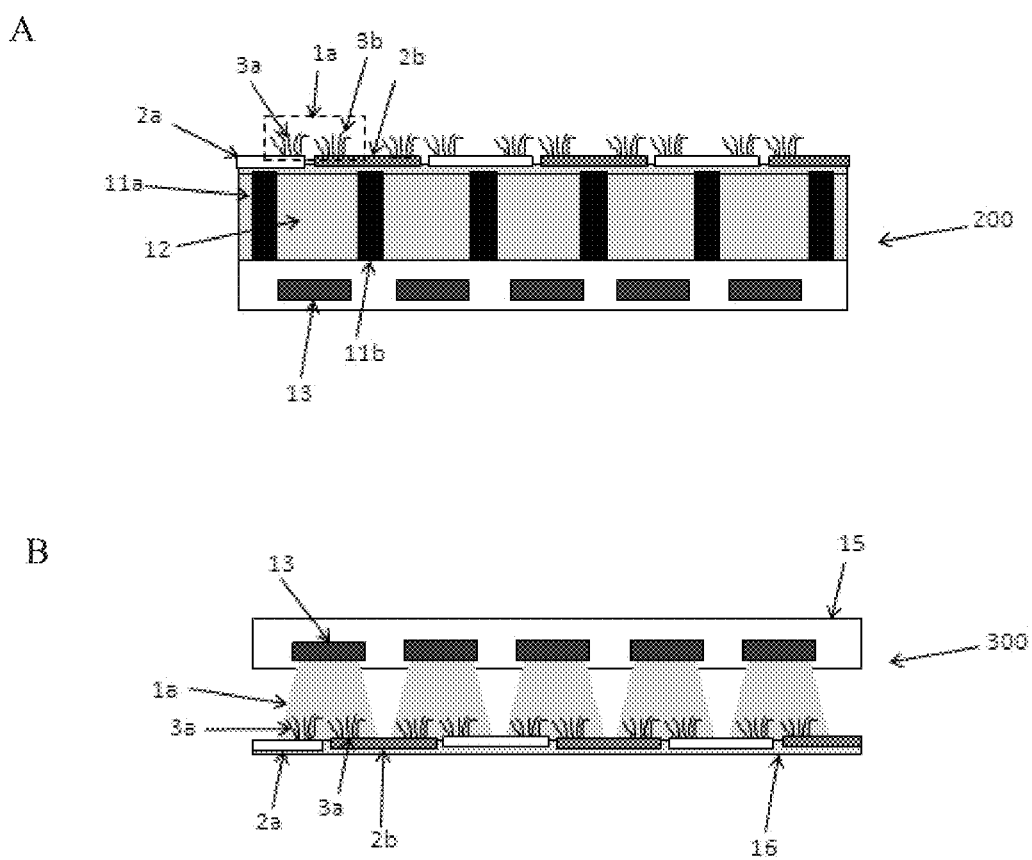
FIG. 3 shows side views of (A) an array of pixels and an array of electrically responsive pads integrated into a substrate, and (B) an array of pixels in a detection unit positioned to detect electrically responsive pads on a substrate that is separate from the detection unit.

FIG. 3 shows side profile views of two detection apparatus that have an array of pixels and an array of responsive pads configured as diagrammed in FIG. 2. Panel A shows an integrated apparatus 200 wherein the array of pixels and the array of responsive pads are fixed on a substrate. The pixels are optically coupled to detection zones via light pipes in the substrate. For example, signal from nucleic acid clusters 3a and 3b in detection zone 1a passes through light pipe 12 to reach pixel 13. The light pipe is bounded by vertical curtains 11a and 11b that prevent cross talk of optical signals between pixels. Nucleic acid cluster 3a is attached to responsive pad 2a and cluster 3b is attached to pad 2b. Pads 2a and 2b can be independently actuated to allow super resolution imaging of clusters 3a and 3b. As shown in Panel A, at least a portion of each pad is in the detection zones for two pixels. For embodiments that use fluorescence detection, light pipe 12 can include an optical filter that blocks excitation radiation from reaching the pixel 13. An advantage of the configuration shown in FIG. 3, Panel A is that the array of pixels and array of responsive pads are positionally fixed relative to each other. This design does not require alignment and focusing devices used in multi-component designs where the two arrays can move relative to each other.

Panel B of FIG. 3 shows a detection apparatus 300 having a camera component 15 that is separated in space from the substrate that is to be detected 16. In such a configuration the camera component 15 can be moved relative to the array of responsive pads that is located on substrate 16, for example, to achieve a desired focus, resolution or alignment. Pixel 13 is directed to substrate 16 and has a detection area 1a that includes two nucleic acid clusters 3a and 3b on separate responsive pads 2a and 2b, respectively. The camera in Panel B is configured for epifluorescent detection when an excitation assembly is present, for example, at a position that excites the nucleic acid clusters from the same side of substrate 16 that is observed by the pixels. Again, pads 2a and 2b can be independently actuated to allow super resolution imaging of clusters 3a and 3b. At least a portion of each of the pads is in the detection zones for two pixels.

Figure 4:
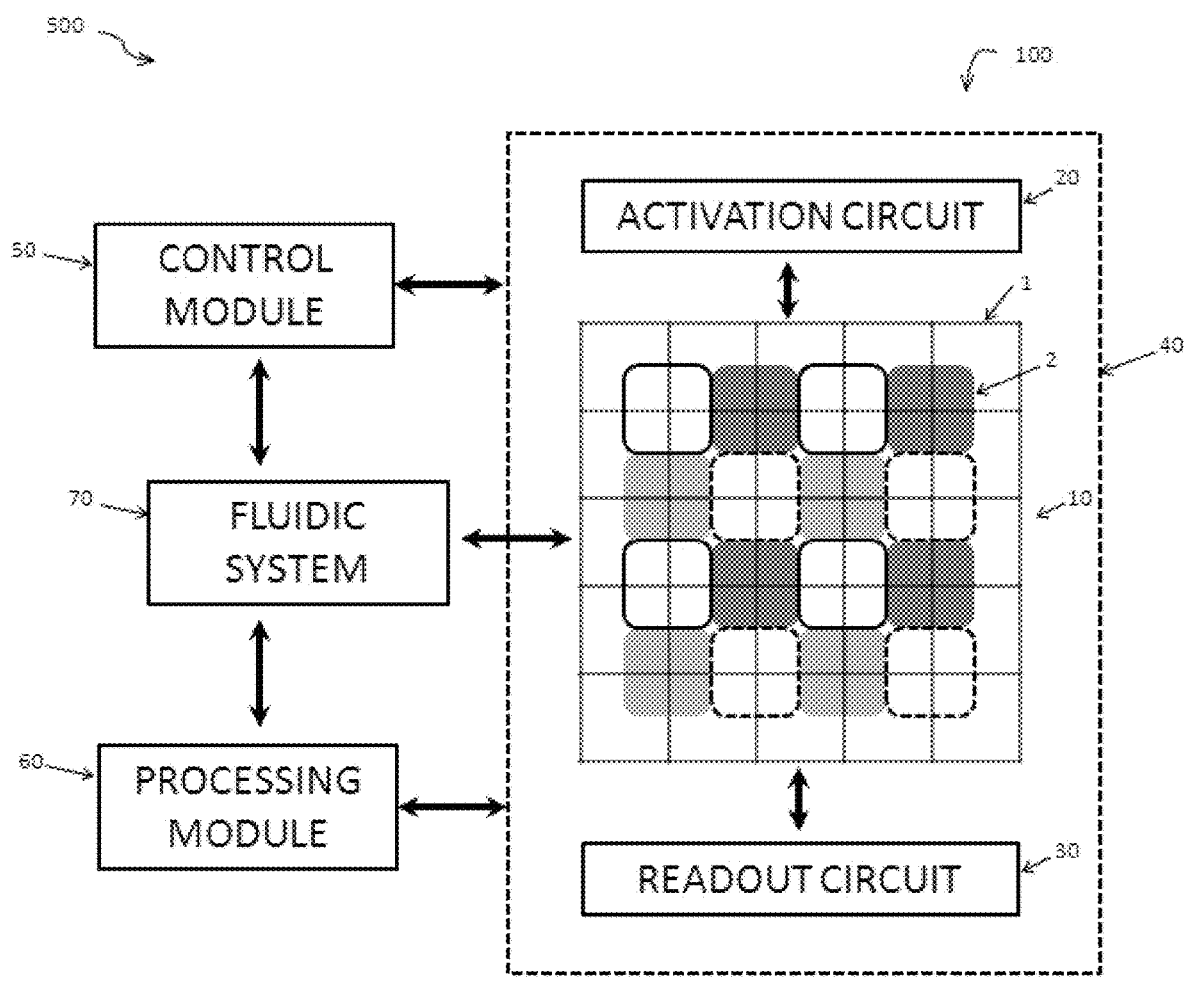
FIG. 4 shows a diagram of a detection system.

An apparatus of the present disclosure can include an activation circuit to actuate changes in the characteristics of responsive pads in an array of pads. FIG. 4 shows a diagrammatic representation of a detection apparatus 100 including a detection module 10 (including an array of reactive pads 2 and an array of pixel detection areas 1), an activation circuit 20 configured to actuate changes in each of the responsive pads 2 and, optionally, to receive feedback regarding the state of each pad 2. As set forth previously herein, the activation circuit can be configured to individually address and actuate each of the responsive pads. The activation circuit can produce changes in any of a variety of characteristics at or near the responsive pads including, but not limited to, presence or absence of electric charge; positive, negative or neutral polarity of electric charge; strength of electric field; shape of electric field; presence or absence of electric current; direction of electric current; strength of electric current; type of electric current (e.g. DC and/or AC); shape for AC current waveform; frequency or magnitude of AC current; magnetic state; presence or absence of a magnetic dipole; chemical properties at the surface such as pH, redox potential, hydrophobicity, hydrophilicity, presence of a reactive species or absence of a reactive species; and the like.

Thus, an activation circuit can place responsive pads into different states. As used herein, the term "different" or "differential," when used in reference to a responsive pad, means that the pad has at least one characteristic that is absent at another pad or that is not present to the same degree as at another pad. The characteristic is typically responsive to an activation circuit or other device that actuates change at the pad. For example, pads can be different with respect to changes in the characteristics set forth herein, for example, with regard to an activation circuit. It will be understood that the phrase "a different electric field" can be used to refer to the presence or absence of an electric field, such that a pad that has no electric field can be considered to have a different electric field from a pad that has an electric field unless explicitly stated to the contrary. Other different states include, for example, changes in hydrophobicity and hydrophilicity. Such changes in state can occur due to electrowetting and other techniques known in the art for manipulating droplets examples of which are set forth in US Pat. App. Pub. No. 2013/0116128 A1, which is incorporated herein by reference.

In particular embodiments an activation circuit is configured to apply an electric field at first and second pads in an array of pads (for example at two pads in the detection zone of a single pixel). The activation circuit can be configured to apply a different electric field at the first pad compared to the second pad, and the activation circuit can have a switch to selectively alter the electric field at the first pad compared to the second pad.

As used herein, the term "selectively alter" means to alter one thing (e.g. a first pad) to a greater degree than another thing (e.g. a second pad). In some cases selective alteration can be achieved by turning one thing on and another thing off. However, it is also possible to make a selective alteration without turning one of the things on and instead reducing or increasing an actuatable characteristic of one of the things relative to the other thing. Selective alteration can result in changes for any of the characteristics set forth herein, for example, above with regard to an activation circuit. For example, an activation circuit can be configured to apply (or relatively increase) electric field at a first pad while preventing (or relatively decreasing) electric field at a second pad, and a switch can be configured to prevent (or relatively decrease) electric field at the first pad while applying (or relatively increasing) electric field at the second pad. Similarly, an activation circuit can be configured to apply positive electric field at a first pad while applying negative electric field at a second pad, and a switch can be configured to apply negative electric field at the first pad while applying positive electric field at the second pad. As a further example, a pad can be actuated to attract or repel an aqueous droplet or the contents of an aqueous droplet. In particular embodiments a pad is actuated by electrowetting to attract or repel a droplet.

An apparatus of the present disclosure can further include a readout circuit to acquire signals from an array of pixels. The detection apparatus 100 diagrammed in FIG. 4 includes a detection module 10 (including an array of reactive pads 2 and an array of pixel detection areas 1), an activation circuit 20 and a readout circuit 30. The readout circuit 30 can be configured to obtain signal information from the pixel detection areas 1 via the array of pixels. The readout circuit can optionally be configured to alter the gain of individual pixels or to turn pixels on and off in response to the amount of signal received by one or more pixels in the array of pixels.

An apparatus of the present disclosure can be included in a detection system 500 as diagrammed in FIG. 4. The system can include detection apparatus 100 fluidically coupled to a fluidic system 70 and in operative communication with a control module 50 and a processing module 60. The fluidic system 70 can be configured to deliver fluid reagents used in a detection method that occurs in the detection apparatus 10. In some embodiments, such as those using sequencing-by-synthesis as set forth below, the fluidic system can deliver reagents in repeated cycles. Repeated cycles of fluid delivery can also be useful for other applications where polymeric molecules are synthesized or sequenced, or for other applications. Alternatively, a fluidic system can be configured for non-cyclic delivery of reagents to a given array of pads or at least for a given sample present on the array of pads. Examples of fluid systems that are coupled to biological arrays and that can be readily adapted to deliver fluids to an array of pads set forth herein are described in US Pat. App. Pub. No. US 2010/0009871 A1; US Pat. App. Pub. No. 2012/0270305 A1 and U.S. patent application Ser. No. 13/766,413, (published as US Pat. App. No. 2013/0260372 A1) each of which is incorporated herein by reference. Particularly useful fluidic systems are those that move fluid droplets to and from detection areas via electrowetting or other techniques as described, for example, in U.S. patent application Ser. No. 13/670,318 (published as US Pat. App. Pub. No. 2013/0116128 A1), which is incorporated herein by reference.

The control module 50 can be configured to direct the readout circuit 30 to acquire signals from each of the pixel detection areas 1 during a sensing period. The control module 50 can also communicate with the activation circuit 20 to direct actuation of responsive pads during the sensing period. The communication from the control module 50 can direct the activation circuit to switch the actuation at the responsive pads. In an exemplary embodiment of the system diagrammed in FIG. 4, the control module 50 can direct the readout circuit 30 to acquire signals from each of the pixels during a sensing period, direct the activation circuit 20 to apply a different electric field at the first pad compared to the second pad, during the sensing period, and direct the activation circuit to switch to selectively alter the electric field at the first pad compared to the second pad, during the sensing period.

As used herein, the term "sensing period" means a time frame, whether continuous or discontinuous, during which signal is collected. Accordingly, a control module can direct a readout circuit to acquire signals from a pixel continuously during a sensing period, or alternatively, the control module can direct the readout circuit to toggle the pixel between an on-state and an off-state during a sensing period. Similarly, the gain at a pixel can be increased or decreased during a sensing period.

Control module 50 can be further configured to communicate with the fluidic system 70. The control module 50 can provide instructions to the fluidic system to direct reagent delivery from a particular reservoir, or other fluidic component, to the detection apparatus 100. When multiple fluids are to be delivered, for example as is the case for a sequencing-by-synthesis protocol, the control module 50 can direct the sequence of fluid components delivered to the detection apparatus 100. Generally, control module 50 can also direct the amount of fluid delivered at a particular step of a protocol, the duration of delivery of a particular fluid, the temperature for a particular fluid, the rate of fluid delivery (e.g. via changes in fluid pressure), and the like. The control module 50, being in communication with the fluidic system 70, the readout circuit 30, the detection module 10, and the activation circuit 20 can coordinate super resolution detection of a plurality of target analytes that are chemically manipulated in an array-based platform. An example of such a platform is one using a sequencing-by-synthesis technique.

In particular embodiments, the control module 50 can also be configured to receive feedback from the activation circuit 20, readout circuit 30, fluidic system 70 or detection module 10. Feedback from one or more of these components can be used to modify directions sent to the component(s) from which feedback was received or another component of the system. Thus, the control module can assess the overall condition of the system and modify function to achieve desired output or activity. Exemplary algorithms and configurations for assessing and modifying function of an array-based detection system are described in U.S. Pat. No. 8,244,479, which is incorporated herein by reference. In particular embodiments, the control module 50 can also be in communication with the processing module 60, to send directions or receive feedback pertaining to the functions of the processing module 60.

A processing module 60 that is included in a system 500 of the present disclosure can be in communication with a readout circuit 30. The processing module 60 can receive signals from the readout circuit 30 and modify the signals to create data in a desired format. Taking an SBS system as an example, the processing module 60 can determine the identity of a nucleotide that is incorporated at a particular nucleic acid cluster from electrical signals obtained by a pixel during a sensing period and from a schedule of actuation periods for two or more pads that were in the detection zone of the pixel during the sensing period. The processing module 60 can further include algorithms to manipulate data to provide a desired output that can be communicated to a user. For example, data can be used to determine presence or absence of a target analyte (e.g. presence of a nucleic acid sequence or presence of a single nucleotide polymorphism in a sequence), amount of a target analyte (e.g. ploidy level for a gene sequence or expression level for an RNA sequence), structure of a target analyte (e.g. nucleotide sequence of a nucleic acid), chemical reactivity of a target analyte (e.g. binding affinity between receptor and ligand or kinetics of reaction for an enzyme) or the like.

Processing module 60 can also be configured to send directions to other components of the system based on data obtained or processed. For example, processing module 60 can determine when enough information has been obtained from a sample that further manipulation and/or observation of the sample can be stopped. Directions can then be sent to the detection apparatus, for example via the control module, to cease or pause data acquisition.

The various components of system 500 or other system of the present disclosure can be present in a single unit, for example, having a relatively small footprint. Alternatively, the components can be distributed, for example, in a network that includes data connections and in some cases fluidic connections. In some embodiments, information processing modules can be distributed in a computer network that is connected to other components of the system. In some cases one or more of the processing modules can be cloud-based. Exemplary, cloud-based systems for processing sequencing data and that can be adapted for use in a system or method of the present disclosure are described in U.S. patent application Ser. No. 13/790,596 (published as US Pat. App. Pub. No. 2013/0275486 A1) and Ser. No. 13/790,623 (published as US Pat. App. Pub. No. 2013/0274148 A1), each of which is incorporated herein by reference.

A system provided by the present disclosure can be used for sequencing nucleic acids. The system can include (a) a detection apparatus having (i) an array of electrically responsive pads on a substrate surface; (ii) an array of pixels, wherein each pixel in the array has a detection zone on the surface that includes a subset of four of the pads; and (iii) an activation circuit to apply an electric field to the pads in the subset individually, wherein the activation circuit is configured to apply a different electric field at a first pad of the subset compared to the other pads of the subset; (b) a readout circuit to acquire signals from the array of pixels; (c) a control module that directs the readout circuit to acquire signals from each of the pixels during a sensing period and that directs the activation circuit to sequentially apply different electric fields at the four pads during the sensing period; and (d) a processing module that correlates (i) the signals acquired from the pixels during the sensing period and (ii) the sequential application of the different electric fields at the four pads during the sensing period, in order to distinguish a sequence of signals for each of the pads.

The control module and processing module of a nucleic acid sequencing system can be configured to carry out a sequencing-by-synthesis (SBS) protocol. In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different features on an array of responsive pads set forth herein can be subjected to an SBS technique under conditions where events occurring for different templates can be distinguished using super resolution imaging.

Flow cells provide a convenient format for housing an array of nucleic acid clusters located on responsive pads that are subjected to an SBS technique that involves repeated delivery of reagents in cycles. Exemplary flow cells are set forth above and in references cited above. To initiate a first SBS cycle, one or more labeled nucleotides, DNA polymerase, etc., can be flowed into/through a flow cell that houses an array of nucleic acid clusters that have been hybridized to a sequencing primer. Those sites of an array where primer extension causes a labeled nucleotide to be incorporated can be detected. Optionally, the nucleotides can further include a reversible termination property that terminates further primer extension once a nucleotide has been added to a primer. For example, the labeled nucleotide that is contacted with the nucleic acid clusters can have a reversible terminator moiety that gets added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection system components that can be readily adapted for use in a system of method of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored by detecting photons released during this chemiluminescent reaction. Accordingly, excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both sequencing-by-ligation and sequencing-by-hybridization procedures, target nucleic acids (or amplicons thereof) that are present at sites of an array are subjected to repeated cycles of oligonucleotide delivery and detection. Typically, the oligonucleotides are fluorescently labeled and can be detected using fluorescence detectors similar to those described with regard to SBS procedures herein or in references cited herein.

A fluidic system used in a system or method set forth herein can store and deliver one or more of the reagents or fluid components set forth above in the context of target nucleic acid capture, amplification or nucleotide sequencing protocols. For example, the reagents can be stored in appropriate reservoirs prior to delivery to a flow cell or substrate such as one already having an array of nucleic acids. Furthermore, a detection apparatus can include a nucleic acid feature (e.g. a nucleic acid cluster) having an intermediate species produced by one of the steps (e.g. a primer attached to a labeled and reversibly terminated nucleotide, or a primer attached to a labeled nucleotide that lacks a terminator, or a nucleic acid attached to a polymerase and/or nucleotide). The nucleic acid feature can in turn be attached to a responsive pad that is in one of the states exemplified herein for producing a signal to be detected or in a state for inhibiting a signal from being detected at the nucleic acid feature. Different features can have differential properties such as different priming sites or different primers hybridized to the features.

A processing module 60 that is included in a sequencing system can be configured to correlate (i) the signals acquired from the pixels during the sensing period, (ii) the sequential activation of different pads during the sensing period, and (iii) the sequence of reagents delivered to the substrate in order to distinguish a sequence of signals for each of the pads and to distinguish a sequence of reagents that produce the signals at each of the pads. The nucleotide sequence of nucleic acid features at each pad can in turn be determined from this correlation. The nucleotide sequences or the signal data can be exported to another processing device for sequence analysis.

The present disclosure also provides a detection apparatus that includes (a) an array of responsive pads on a substrate surface, wherein each responsive pad includes a nucleic acid feature of a plurality of nucleic acid features in the array, wherein a first subset of nucleic acid features in the plurality of nucleic acid features have a first universal sequence and different target sequences, wherein a second subset of nucleic acid features in the plurality of nucleic acid features have a second universal sequence and different target sequences, wherein the first universal sequence is different from the second universal sequence; (b) an array of pixels, wherein each pixel in the array has a detection zone on the surface that includes at least two nucleic acid features of the plurality of nucleic acid features, the at least two nucleic acid features including a nucleic acid from the first subset of nucleic acid features and a nucleic acid from the second subset of nucleic acid features; and (c) an activation module to alter a characteristic of a pad in the first subset and of a pad in the second subset, wherein the activation module is configured to apply a different characteristic at the pad in the first subset compared to the pad in the second subset, and wherein the activation module has a switch to selectively alter the characteristic at the pads in the first and second subsets.

Optionally, the detection apparatus can be included in a nucleic acid sequencing system that also includes (I) a readout circuit to acquire signals from the array of pixels; (II) a control module that directs the readout circuit to acquire signals from each of the pixels during a sensing period and that optionally directs the activation circuit to sequentially actuate different responsive pads in each of the detection zones during the sensing period; and (III) a processing module that optionally correlates (i) the signals acquired from the pixels during the sensing period and (ii) the sequential actuation of the different responsive pads during the sensing period, in order to distinguish a sequence of signals for each of the pads.

The present disclosure further provides a method of detecting analytes. The method can include the steps of (a) providing a detection apparatus having an array of electrically responsive pads and an array of pixels, wherein each pixel in the array has a detection zone that includes a subset of at least two of the electrically responsive pads, wherein the two pads include different target analytes, respectively; (b) acquiring signals from each of the pixels while selectively applying an electric field at a first of the two pads to preferentially produce signal from a first of the different target analytes compared to a second of the target analytes, thereby preferentially acquiring signals from the first of the target analytes compared to the second of the target analytes; and (c) acquiring signals from each of the pixels while selectively applying an electric field at the second of the two pads to preferentially produce signal from the second of the different target analytes compared to the first of the target analytes, thereby preferentially acquiring signals from the second of the target analytes compared to the first of the target analytes.

As used herein, the term "preferentially acquire," when used in reference to a signal, means to detect more signal from one source (e.g. from a first target analyte at a first pad) than from another source (e.g. a second target at a second pad). In some cases preferential acquisition can be achieved by detecting signal only from one source and not from another. However, it is also possible to detect more of a signal or a different type of a signal, from one source compared to another when preferentially acquiring signal.

A method set forth herein can be carried out using an apparatus or system exemplified herein. However, other suitable apparatus or systems can be used as desired for a particular application of the methods. In particular embodiments, a detection method can include a step of acquiring signals from a pixel while selectively actuating a first of at least two pads that are in the detection zone of the pixel. This can allow signal to be preferentially produced from a first target analyte that is at one of the pads compared to a second target analyte that is at the other pad. Thus, signals can be preferentially acquired from the first target analytes even when the second target analytes are in the field of view of the pixel.

In one exemplary embodiment, the target analytes can produce signal when the pads to which they are attached are actuated to produce an electric field. This can be demonstrated for a pad that attracts a label to the target analyte when the electric field is turned on. In this case, a target analyte that is present at a pad that is not activated to produce the electric field (or at a pad that produces a substantially weaker field or at a pad that is activated to produce a field of opposite polarity) will not produce signal and will not be detected. The electric fields at the two pads can be switched to change the pad from which signal is detected by the pixel. As such, acquiring signal from the pixel and accounting for the schedule of states for the pads can be used to achieve super resolution detection of the different target analytes that are simultaneously in the detection zone of the pixel. Thus, different target analytes that are simultaneously present in the detection zone of a single pixel can be distinguished by selective spatial activation (or inhibition) of signal generation during detection. Any of a variety of labels and detectable moieties exemplified elsewhere herein can be used similarly.

Figure 5:
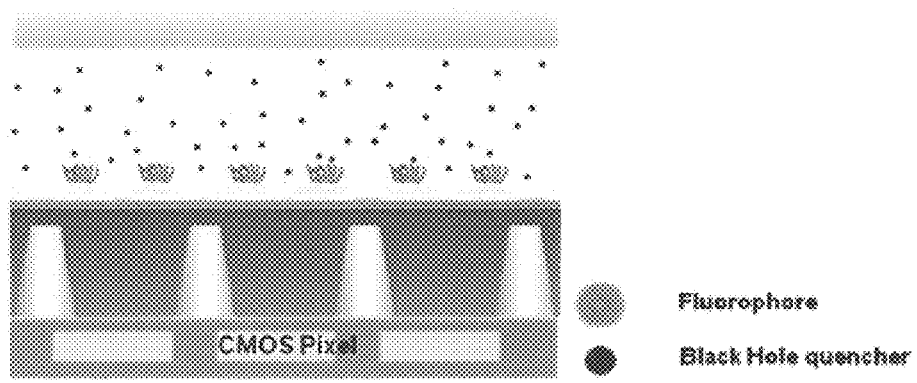
FIG. 5 shows a diagram of a detection apparatus that differentially detects fluorescent analytes from two pads in the detection zone of a single pixel by selectively attracting a fluorescence quencher to one of the pads.
Figure 5:
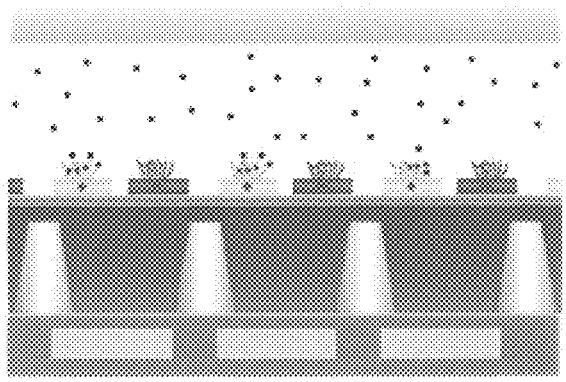
Figure 5:
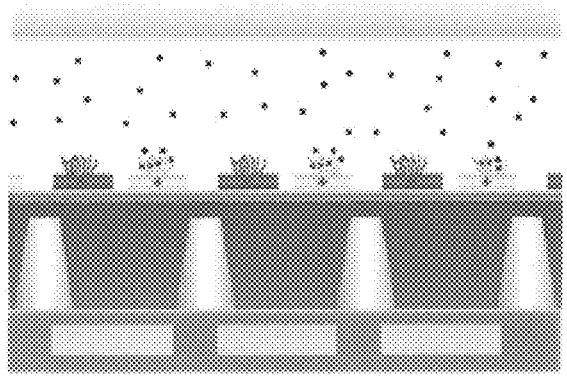

In an alternative embodiment, the target analytes can be prevented or inhibited from producing signal when the pads to which they are attached are actuated to produce an electric field. This can be demonstrated for a pad that has a label present and that attracts a quencher when the electric field is turned on. FIG. 5 provides a diagrammatic representation of a detection apparatus in three different states. In a first state (Panel A) neither of the two pads is charged and the quencher (e.g. black hole quencher) is not attracted to fluorescently labeled clusters that are present at either of the pads. Thus, clusters at both pads are fully capable of producing fluorescent signals. Panel B shows the state where the pad at the left side of each detection zone is positively charged, thereby creating an electric field that attracts the negatively charged black hole quencher to the cluster. As such, the nucleic acid clusters at the left side pads will be quenched and the pixel will detect little to no signal from these clusters. However, the right side pads will produce "unquenched" signal that is detected by the pixel. As demonstrated by Panel C, the electric fields at the two pads can be switched to change the cluster from which signal is detected by each pixel, thereby allowing super resolution imaging. In this case, the pads on the right attract quencher, decreasing or preventing signal detection, and the pads on the left release quencher to produce fluorescent signal that is detectable by the pixel. Again, any of a variety of labels and detectable moieties exemplified elsewhere herein can be used similarly.

Further by way of example, selectively applying an electric field at the first of two pads in a method of the present disclosure can attract a fluorescence quencher to the first pad to preferentially quench fluorescence at the first pad, thereby preferentially producing signal at the second of the two pads. In this example a switch can be used to selectively apply the electric field at the second pad to attract the fluorescence quencher to the second pad to preferentially quench fluorescence at the second pad, thereby preferentially producing signal at the first pad.

In a second example, selectively applying an electric field at the first pad in a method of the present disclosure can attract a fluorescent label to the first pad to preferentially produce fluorescence at the first pad compared to the second pad. In this second example, a switch can be used to selectively apply the electric field at the second pad to attract the fluorescent label to the second pad to preferentially produce fluorescence at the second pad compared to the first pad.

In a third example, selectively applying an electric field at the first pad can induce luminescence from electrochemical luminescence labels at the first pad to preferentially produce luminescence at the first pad compared to the second pad. In this third example, a switch can be used to selectively apply the electric field at the second pad to induce luminescence from electrochemical luminescence labels at the second pad to preferentially produce luminescence at the second pad pads compared to the first pad.

Selective activation that allows super-resolution imaging need not occur during a detection step or even during a sensing period. For example, prior to the sensing period of a solid-phase SBS protocol, subsets of target nucleic acids in a library can be selectively captured at pads of a solid support, selectively amplified to form features on pads of a solid support or selectively hybridized to an SBS primer.

Accordingly, provided herein is a method of detecting target nucleic acids, including the steps of (a) providing a substrate comprising an array of pads, the array of pads including a first subset of the pads and a second subset of the pads; (b) delivering a first solution to the substrate, wherein the first solution includes a first plurality of different target nucleic acids that selectively attach to the first subset of pads compared to the second subset of pads; (c) delivering a second solution to the substrate, wherein the second solution includes a second plurality of different target nucleic acids that selectively attach to the second subset of pads compared to the first subset of pads; and (d) detecting the substrate using an apparatus having an array of pixels, wherein each pixel in the array has a detection zone that includes (i) at least one of the target nucleic acids that is attached to a pad of the first subset of pads, and (ii) at least one of the target nucleic acids that is attached to a pad of the second subset of pads.

For embodiments that include delivery of a first solution and a second solution to a substrate, it will be understood that the solutions can be delivered simultaneously as a preformed single solution or they can be delivered in a way that the solutions mix to form a single solution in the presence of the substrate. Alternatively, the first and second solutions can be separate solutions that are delivered to a substrate sequentially. The first solution can be removed from contact with the substrate prior to delivery of the second solution. Optionally, the substrate can be treated with one or more wash solutions between delivery of the first solution and delivery of the second solution.

A first plurality of nucleic acids and second plurality of nucleic acids can be differentially captured at two or more pads on a substrate based on differential properties of the nucleic acids, differential properties of the pads or both. An exemplary property of the nucleic acids that can be exploited for differential capture include, but are not limited to, presence of particular sequence regions (e.g. a priming sequence, capture sequence, or the like). These sequence regions can facilitate capture via hybridization to complementary sequences present on capture probes that are located at each pad. Other exemplary properties include, but are not limited to, presence of a binding moiety (e.g. a ligand or receptor), charge, mass, length (i.e. number of nucleotides in the sequence), secondary structure (e.g. presence of single stranded or double stranded domains), or the like. Differential properties of the pads can include actuated or activated properties such as those set forth elsewhere herein, the sequence of attached nucleic acid capture probes, presence or absence of nucleic acid adapters, presence or absence of a ligand or receptor, etc.

In some embodiments, the first plurality of nucleic acids may have a first universal sequence that is different from a second universal sequence that is present in the nucleic acids of the second plurality of nucleic acids. Subsets of pads having capture probes that are complementary to the respective universal sequences will provide differential capture.

Alternatively, subsets of unique capture probes need not be used. Rather, differential capture can be achieved by actuating a particular subset of pads for capture in the presence of a first solution of nucleic acids and against capture in the presence of a second solution of nucleic acids. Thus, selective capture can be achieved by sequential treatment of an array of responsive pads with different nucleic acid solutions under controlled actuation of the pads.

In a further embodiment, differential capture of target nucleic acids can be achieved by differential pretreatment of an array of responsive pads prior to contacting the array with target nucleic acids. An exemplary pretreatment is the modification of different responsive pads to attach adapter nucleic acids. This can be achieved by actuating a particular subset of pads for modification in the presence of a first solution of adapters and against modification in the presence of a second solution of adapters. Thus, selective modification can be achieved by sequential treatment of an array of responsive pads with different adapter solutions under controlled actuation of the pads. The adapters can be, for example, nucleic acids having a first sequence region that is complementary to capture probes on the pads and a second sequence region that is complementary to a universal sequence on a particular population of target nucleic acids. Thus, in the example above, the adapters in the first solution can have a capture probe complement sequence and a first universal sequence complement sequence while the adapters in the second solution have the same capture probe complement sequence and a second universal sequence complement. Following differential treatment of the responsive pads to form adapter-modified pads, the adapter modified pads can be treated with a first and second plurality of target nucleic acids having first and second universal sequences, respectively, to thereby achieve differential capture of the target nucleic acids.

Exemplary reagents and techniques for modifying surfaces with adapters and using the modified surfaces to attach target nucleic acids are set forth in U.S. Pat. App. No. 61/928,368, which is incorporated herein by reference. Such reagents and methods can be used in a method or composition set forth herein.

Although hybridization based capture is exemplified above, it will be understood that capture can be mediated by other physical and chemical interactions between nucleic acids and pads including, but not limited to, receptor-ligand interactions, chemical crosslinking, covalent bonds, ionic interactions, magnetic interactions (e.g. Nucleic acids can be attached to beads that are held to pads via magnetism), or the like.

An array of features having two different features in the detection zone of the same pixel, and wherein the different features have nucleic acids with different universal sequences, can be detected by sequentially (a) hybridizing first primers to the first universal sequence of the target nucleic acids that are attached to a first subset of pads; (b) extending the first primers by addition of at least one nucleotide; (c) hybridizing second primers to the second universal sequence of the target nucleic acids that are attached to a second subset of pads; and (d) extending the second primers by addition of at least one nucleotide, whereby signals are detected from the target nucleic acids that are attached to the first subset of responsive pads at a different time than when signals are detected from the target nucleic acids that are attached to the second subset of responsive pads.

Optionally, a method of the present disclosure can include a step of amplifying first target nucleic acids that are attached to pads of a first subset of pads using primers that are complementary to a first universal sequence that is present on the first target nucleic acids, and amplifying second target nucleic acids that are attached to pads of the second subset of pads using primers that are complementary to a second universal sequence that is present on the second target nucleic acids. Amplification can be carried out by solid phase amplification methods set forth herein such as bridge amplification or solid-phase PCR. Accordingly, amplification can be selectively achieved when the first and second universal sequences are complementary to different amplifications primers.

Selective amplification at different features can be facilitated by the presence of different priming sequences at each feature, for example as set forth above, and/or by selective actuation of pads to attract or repel reagents used for amplification. For example, selective actuation can be used to selectively hybridize amplification primers to target nucleic acids that are attached to a first subset of responsive pads compared to target nucleic acids at other pads. A method set forth herein can include a step of contacting a solution of first amplification primers with a substrate while selectively actuating a first subset of responsive pads, wherein the first amplification primers selectively hybridize to a first plurality of different target nucleic acids attached to the first subset of responsive pads compared to a second plurality of different target nucleic acids attached to a second subset of pads. Continuing with the example, the method can optionally include a step of contacting a solution of second amplification primers with the substrate while selectively actuating the second subset of responsive pads in the array, wherein the second amplification primers selectively hybridize to the second plurality of different target nucleic acids compared to the first plurality of different target nucleic acids. The first amplification primers can have the same sequence as the second amplification primers. Alternatively, the first amplification primers can have a different sequence compared to the second amplification primers.

Selective amplification can facilitate selective detection when a first target nucleic acid is selectively amplified to allow detection in the zone of a pixel followed by selective amplification of the a second target nucleic acid that is detected by the same pixel in the same detection zone.

In particular embodiments, a method of detecting nucleic acids can include the steps of (a) providing a substrate comprising an array of pads, the array of pads including a first subset of the pads and a second subset of the pads; (b) contacting a first solution with the substrate while selectively actuating the first subset of responsive pads in the array, wherein the first plurality of different target nucleic acids attach to responsive pads of the first subset that are selectively actuated; (c) contacting a second solution with the substrate while selectively actuating the second subset of responsive pads in the array, wherein the second plurality of different target nucleic acids attach to responsive pads of the second subset that are selectively actuated; and (d) detecting the substrate using an apparatus having an array of pixels, wherein each pixel in the array has a detection zone that includes (i) at least one of the target nucleic acids that is attached to a pad of the first subset of pads, and (ii) at least one of the target nucleic acids that is attached to a pad of the second subset of pads. Optionally, the target nucleic acids include a universal sequence that is the same for nucleic acids of the first and second plurality. The universal sequence of the target nucleic acids can, in some embodiments, hybridize to capture probes attached to the first and second subset of pads.

In some embodiments, a method of detecting nucleic acids can include the steps of (a) providing a substrate comprising an array of pads, the array of pads including a first subset of the pads and a second subset of the pads; (b) contacting a solution of adapter nucleic acids with the substrate while selectively actuating one or both of the subsets of responsive pads, wherein the adapter nucleic acids attach to responsive pads of the one or both subsets that are selectively actuated; (c) contacting a first solution with the substrate, wherein the first plurality of different target nucleic acids attach to responsive pads of the first subset; (d) contacting a second solution with the substrate, wherein the second plurality of different target nucleic acids attach to responsive pads of the second subset, wherein the responsive pads of one or both of the first and second subset are attached to the adapter nucleic acids; and (e) detecting the substrate using an apparatus having an array of pixels, wherein each pixel in the array has a detection zone that includes (i) at least one of the target nucleic acids that is attached to a pad of the first subset of pads, and (ii) at least one of the target nucleic acids that is attached to a pad of the second subset of pads.

One or more of the adapters used in a method set forth herein can include a universal sequence complement that is in turn useful for hybridizing to a universal sequence of one or more target nucleic acids. Thus, an adapter can serve to mediate capture of target nucleic acids to desired pads or features of an array set forth herein. Taking the embodiment set forth above as an example, the target nucleic acids in the first plurality can have a first universal sequence and the target nucleic acids in the second plurality can have a second universal sequence that is different from the first universal sequence. The first target nucleic acids can be selectively attached to the first subset of pads due to the first universal sequences hybridizing to the first adapter nucleic acids that are attached to the first subset of pads. Similarly, the selective attachment of the second target nucleic acids to the second subset of pads can involve the second universal sequences hybridizing to the second adapter nucleic acids that are attached to the second subset of pads, wherein the first adapter nucleic acids have a different sequence from the second adapter nucleic acids.

As set forth previously herein, a method of the present disclosure can be used to determine the nucleotide sequences of a plurality of different nucleic acids. Another useful application is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array of probe features, for example, on pads in an apparatus set forth herein. The methods set forth herein can also be used to determine genotypes for a genomic DNA sample from one or more individual. Exemplary assays for array-based expression and genotyping analysis that can be modified for use in a method set forth herein are described in U.S. Pat. No. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference.

Example I

Fluorescence Quenching Using Direct Electrode Energy Transfer

This example shows that selectively applying an electric field at an electrically responsive pad can quench fluorescent labels or moieties at the pad. To achieve super resolution imaging, a switch can be used to alternately apply electric field at two pads that are in the detection zone of a single pixel. Application of the field can quench fluorescence, for example, via energy transfer between a dipole emitter (e.g. a fluorophore) and a metallic surface. A fluorescently labeled nucleic acid molecule is particularly useful due to the flexibility in the molecule which allows the fluorophore to be pulled closer to the surface (by the field) where quenching is greatest. Other flexible target analytes or those having flexible linkers can be used similarly. Nucleic acids or other fluorescently labeled target analytes can be attached to a surface and surface quenching can be carried out, for example, as described in Rant et al. *Nano Lett.* 4:2441-2445 (2004), which is incorporated herein by reference.

As an alternative to direct surface attachment, a nucleic acid or other target analyte can be attached to a gel material that is present at an electrically responsive pad. Exemplary methods and reactants for attaching nucleic acids to gels are described, for example, in US Pat. App. Pub. No. 2011/0059865 A1, or U.S. patent application Ser. No. 13/784,368, each of which is incorporated herein by reference.

Figure 6:
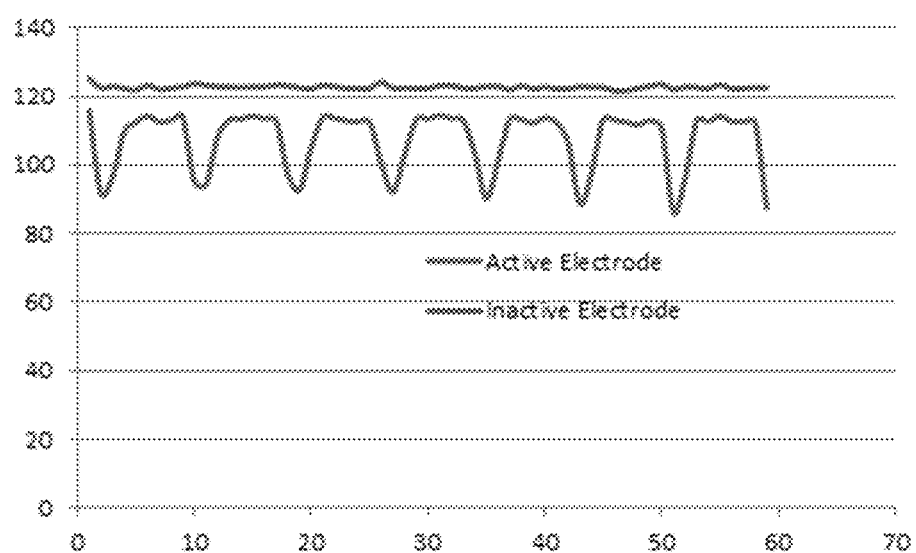
FIG. 6 shows fluorescence intensity modulation when applying multiple cycles of charge on an electrically responsive pad having a fluorescently labeled nucleic acid attached to the pad via a gel.

FIG. 6 shows fluorescence intensity modulation after applying multiple cycles of +/−0.4 V on an electrically responsive pad coated with silane free acrylamide that was grafted to P5 and P7 primers (SFA and P5/P7 primers are described in US Pat. App. Pub. No. 2011/0059865 A1, which is incorporated herein by reference). The P5 and P7 primers were hybridized with HEX dye labeled fluorescent complementary primers. The voltage was pulsed every 2 sec for 0.5 sec and the intensity dipped when the voltage was applied. The intensity modulations appear to be due to fluorescence quenching of the HEX dye label at the electrode surface. In contrast an inactive electrode did not show the intensity fluctuations in fluorescence signal.

Example II

Fluorescence Quenching Using Energy Transfer to Electrically Conductive Polymers This example shows that applying an electric field at an electrically responsive pad that contains electrically conductive polymers in a gel can quench fluorescent labels or moieties that are in the gel.

Transparent conductive polymers, such as poly(3,4-ethylenedioxythiophene) poly(styrenesulfonate) (PEDOT:PSS), polyacetylenes or polyphenylenes, can be embedded in a gel, such as SFA, during the polymerization process. The gel-polymer mix can be polymerized on the responsive pads to provide a porous electrode using conditions previously described for polymerization of SFA (see, US Pat. App. Pub. No. 2011/0059865 A1, which is incorporated herein by reference). A target analyte such as fluorescently labeled nucleic acid can be embedded in the gel. For example, DNA clusters can be grown in the gel-polymer matrix using methods set forth previously herein. Application of an electric field can quench fluorescence, for example, via energy transfer between the fluorophore and the electrically conductive polymers. The energy transfer to the fluorophores can be enhanced, compared to the surface quenching methods of Example I, due to greater proximity between the fluorophores and the conductive polymer. This can in turn lead to more efficient quenching in a conductive polymer-gel compared to on a conductive surface.

To achieve super resolution imaging, a switch can be used to alternately apply electric field at two pads that are in the detection zone of a single pixel. Pads having a fluorescently labeled target analytes in the presence of conductive polymer-gel will be alternately quenched allowing the target analytes to be distinguished by a single pixel having a detection zone that includes the two pads.

Example III

Fluorescence Intensity Modulation with Voltage Sensitive Dyes

This example shows applying an electric field at an electrically responsive pad that contains a target analyte (e.g. a nucleic acid) labeled with a voltage sensitive dye. Applying an electric field can modulate signal from the dye.

An electrically responsive pad is coated with SFA that is grafted to P5 and P7 primers as described in Example I. The P5/P7 primers are hybridized with complementary primers labeled with voltage sensitive dyes such as di-8-ANEPPS (Life Technologies, Carlsbad, Calif.), or ANNINE-6plus (Fromherz et al., *Eur. Biophys. J.* 37: 509-514 (2008)). Application of an electric field to the pad results in increased fluorescence intensity at the pad. Using voltage sensitive dyes, the fluorescence intensity of nucleic acid features clusters can be directly modulated by applying an electric field.

Example IV

Fluorescence Intensity Modulation with Quenchers Tethered to Sequencing Primers

This example shows that applying an electric field at an electrically responsive pad that contains a probe having a quencher moiety tethered to a fluorescent moiety can quench fluorescent signal.

Figure 7:
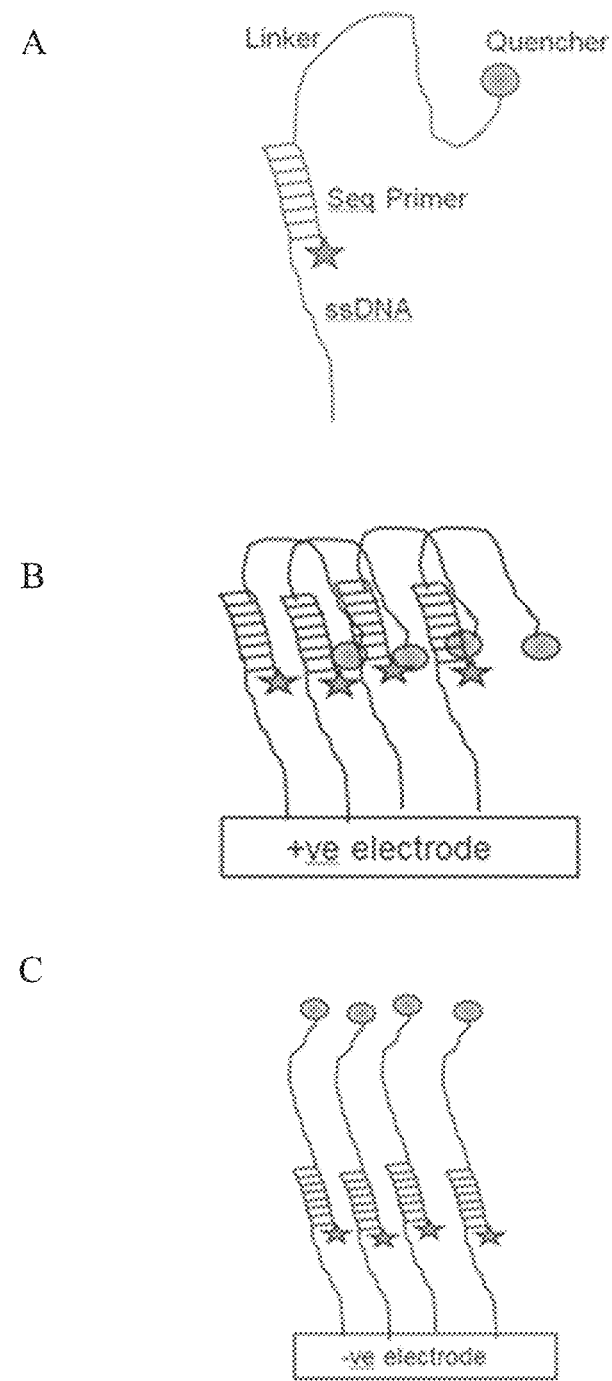
FIG. 7 shows (A) a template nucleic acid hybridized to a primer having a fluorophore at the 3' end and a quencher tethered to the 5' end via a linker arm; (B) the quencher moiety drawn toward the fluorophore by a positive electric field and (C) the quencher moiety repelled away from the fluorophore by a negative electric field.

The strength of quenching is dependent, at least in part, on the intermolecular distance between the quencher and the fluorophore to be quenched. There are multiple approaches to electrically modulate the inter-molecule distance between a quencher and a fluorophore that are bound to the same DNA strand. An example is shown in FIG. 7. Here a quencher is tethered to the 5' end of a sequencing primer using a linker arm. The 3' end of the primer is hybridized to a target sequence and a fluorophore is attached at the 3' terminus, for example, as a result of incorporation of a fluorescently labeled nucleotide in an SBS reaction. A quencher moiety that is appropriately charged at working pH, can be electrically repelled or attracted towards the electrodes by a field of opposite polarity. This results in local increase or decrease, respectively, for the quencher in the vicinity of the fluorophore. To achieve super resolution imaging, a switch can be used to alternately apply electric field at two pads that are in the detection zone of a single pixel. Fluorophores at the pads will be alternately quenched allowing the respective target analytes to be distinguished by a single pixel having a detection zone that includes the two pads.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method comprising:
   selectively applying an electric field at a first pad of an array of electrically responsive pads on a substrate surface of a detection apparatus, where the detection apparatus further comprises an array of detection pixels, wherein each detection pixel in the array of detection pixels has a detection zone on the surface, each detection pixel configured to simultaneously observe a subset of at least two of the array of electrically responsive pads;
   acquiring signals from each of the detection pixels while selectively applying the electric field at the first pad;
   selectively applying an electric field at a second pad of the array of electrically responsive pads on the substrate surface of the detection apparatus; and
   acquiring signals from each of the detection pixels while selectively applying the electric field at the second pad;
   where acquiring signals from each of the detection pixels while selectively applying the electric field at the first pad preferentially produces signals from a first target analyte compared to a second target analyte, where the first target analyte is different than the second target analyte.

2. The method of claim 1, where acquiring signals from each of the detection pixels while selectively applying the electric field at the second pad preferentially produces signals from the second target analyte compared to the first target analyte.

3. The method of claim 1, wherein the first target analyte and second target analyte each comprise at least two nucleic acid clusters that are included in the detection zone for a single detection pixel, each of the clusters comprises a different nucleotide sequence from the other cluster.

4. The method of claim 1, wherein the first target analyte and second target analyte each comprises fluorescent moieties, and wherein the detection pixels detect emission from the fluorescent moieties.

5. The method of claim 1, wherein each detection zone is square and each electrically responsive pad occurs in a corner of four of the detection zones.

6. The method of claim 1, wherein each of the array of electrically responsive pads comprises a plurality of nucleic acid clusters and each cluster is included in the detection zone for a single detection pixel.

7. The method of claim 1, wherein each of the array of electrically responsive pads comprises a single nucleic acid cluster and the cluster is included in the detection zones for at least two of the detection pixels.

8. The method of claim 1, wherein selectively applying an electric field at the first pad comprises applying a different electric field at the first pad compared to the second pad.

9. The method of claim 1, wherein each of the array of electrically responsive pads comprises a fluorescence quencher, where the first pad comprises the fluorescence quencher at a higher concentration than at the second pad.

10. The method of claim 1, wherein each of the array of electrically responsive pads comprises a fluorescent probe, where the first pad comprises a fluorescent probe at a higher concentration than at the second pad.

11. The method of claim 1, wherein each of the array of the electrically responsive pads comprises electrochemical luminescence labels.

12. The method of claim 1, wherein selectively applying an electric field at the first pad produces more photons at the first pad than at the second pad.

13. The method of claim 1, wherein selectively applying an electric field at the first pad comprises applying no electric field at the second pad.

14. The method of claim 1, wherein selectively applying an electric field at the second pad comprises applying no electric field at the first pad.

15. The method of claim 1, wherein selectively applying an electric field at the first pad comprises applying a positive electric field at the first pad and applying a negative electric field at the second pad.

16. The method of claim 1, wherein selectively applying an electric field at the second pad comprises applying a positive electric field at the second pad and applying a negative electric field at the first pad.

17. The method of claim 1, wherein the array of electrically responsive pads has the same pitch as a pitch of the array of detection pixels.

18. The method of claim 1, wherein the array of detection pixels is in a complementary metal oxide semiconductor (CMOS) sensor.

19. The method of claim 1, further comprising delivering a solution to the substrate surface of the detection apparatus, wherein the solution includes a plurality of different target nucleic acids that selectively attach to the first pad compared to the second pad.

* * * * *